(12) United States Patent
Schultz et al.

(10) Patent No.: US 12,128,115 B2
(45) Date of Patent: *Oct. 29, 2024

(54) COMPOSITIONS FOR CHELATING METALS AT LOW TEMPERATURES

(71) Applicant: UNIVERSITY OF IOWA RESEARCH FOUNDATION, Iowa City, IA (US)

(72) Inventors: Michael K. Schultz, Iowa City, IA (US); Christopher Pigge, Iowa City, IA (US); Mengshi Li, Iowa City, IA (US); Moustafa Gabr, Iowa City, IA (US); Edwin Sagastume, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/051,037

(22) PCT Filed: Apr. 25, 2019

(86) PCT No.: PCT/US2019/029102
§ 371 (c)(1),
(2) Date: Oct. 27, 2020

(87) PCT Pub. No.: WO2019/240884
PCT Pub. Date: Dec. 19, 2019

(65) Prior Publication Data
US 2021/0228749 A1  Jul. 29, 2021

Related U.S. Application Data

(60) Provisional application No. 62/663,671, filed on Apr. 27, 2018.

(51) Int. Cl.
*A61K 51/04* (2006.01)
*A61K 45/06* (2006.01)
*A61K 51/08* (2006.01)

(52) U.S. Cl.
CPC .......... *A61K 51/0482* (2013.01); *A61K 45/06* (2013.01); *A61K 51/0497* (2013.01); *A61K 51/083* (2013.01)

(58) Field of Classification Search
CPC ................ A61K 51/0482; A61K 45/06; A61K 51/0497; A61K 51/083
USPC ....................................... 424/1.69
See application file for complete search history.

(56) References Cited

U.S. PATENT DOCUMENTS

| | | | |
|---|---|---|---|
| 5,310,535 A | 5/1994 | Kruper et al. | |
| 5,435,990 A | 7/1995 | Cheng et al. | |
| 9,579,404 B2 | 2/2017 | Walters | |
| 11,179,484 B2 * | 11/2021 | Schultz | A61K 51/088 |
| 11,191,854 B2 * | 12/2021 | Burak | A61K 51/0497 |
| 11,576,987 B2 * | 2/2023 | Schultz | A61K 51/048 |
| 2008/0193384 A1 | 8/2008 | Willard et al. | |
| 2017/0266304 A1 | 9/2017 | Thaning et al. | |
| 2019/0177345 A1 * | 6/2019 | Larsen | A61P 35/00 |
| 2019/0336623 A1 * | 11/2019 | Tworowska | A61K 47/12 |

FOREIGN PATENT DOCUMENTS

| | | | | |
|---|---|---|---|---|
| WO | WO-9321963 A2 * | 11/1993 | ......... | A61K 51/0478 |
| WO | 2013029616 A1 | 3/2013 | | |

(Continued)

OTHER PUBLICATIONS

Chappell et al. Nucl. Med. Biol. 2000, 27, 93-100. (Year: 2000).*
Arinez-Soriano, J , et al., "Two-step synthesis of heterometallic coordination polymers using a polyazamacrocyclic linker", Crystengcomm 18(22), 4196-4204 (2016).
Corbin, B , et al., "Screening of ligands for redox-active europium using magnetic resonance imaging", Bioorg Med Chem 26(19), 5274-5279 (2018).
Li, M , et al., "Automated cassette-based production of high specific activity peptide-based theranostic radiopharmaceuticals for image-guided radionuclide therapy for cancer", Applied Radiation and Isotopes 127, 52-60 (2017).

(Continued)

*Primary Examiner* — Michael G. Hartley
*Assistant Examiner* — Sean R Donohue
(74) *Attorney, Agent, or Firm* — Viksnins Harris Padys Malen LLP

(57) ABSTRACT

A method of performing a chelating reaction comprising contacting a divalent metal with a compound of Formula (I): or a salt thereof wherein: each of $R^1$-$R^4$ is independently selected from the group consisting of $CH_2COOR^a$ and $CH_2C(=O)NHR^a$; each of $R^5$-$R^{12}$ is independently selected from the group consisting of H and -L-X; each Ra is independently selected from the group consisting of H and -L-X; each L is independently selected from the group consisting of absent and a linking group; and each X is a biological agent; and wherein the contacting occurs at a temperature below about 40° C. to form a chelated composition.

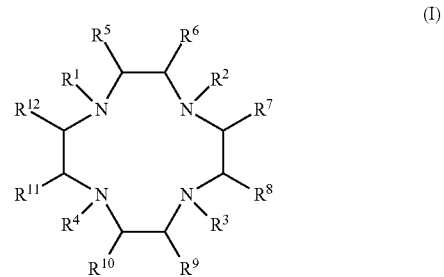

7 Claims, 19 Drawing Sheets

(56) References Cited

FOREIGN PATENT DOCUMENTS

WO           2017165473 A1     9/2017
WO     WO-2017223565 A1 * 12/2017   ........... A61K 31/167

OTHER PUBLICATIONS

Park, J , et al., "Cyclic RGD Peptides Incorporating Cycloalkanes: Synthesis and Evaluation as PET Radiotracers for Tumor Imaging", ACS Medicinal Chemistry Letters 5(9), 979-982 (2014).
Patent Cooperation Treaty , International Search Report and Written Opinion for PCT/US2019/029102, 11 pages, dated Jan. 17, 2020.
Zhang, X , et al., "Macrocyclic chelator assembled RGD multimers for tumor targeting", Bioorganic and Medicinal Chemistry Letters 21, 3423-3426 (2011).

* cited by examiner

VMT-02

Figure 5
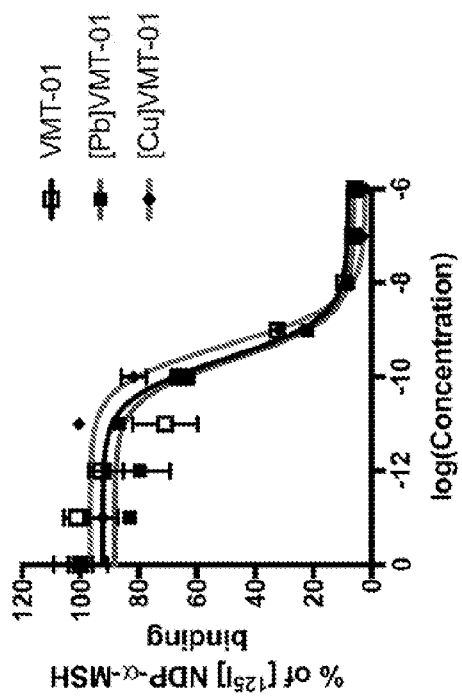
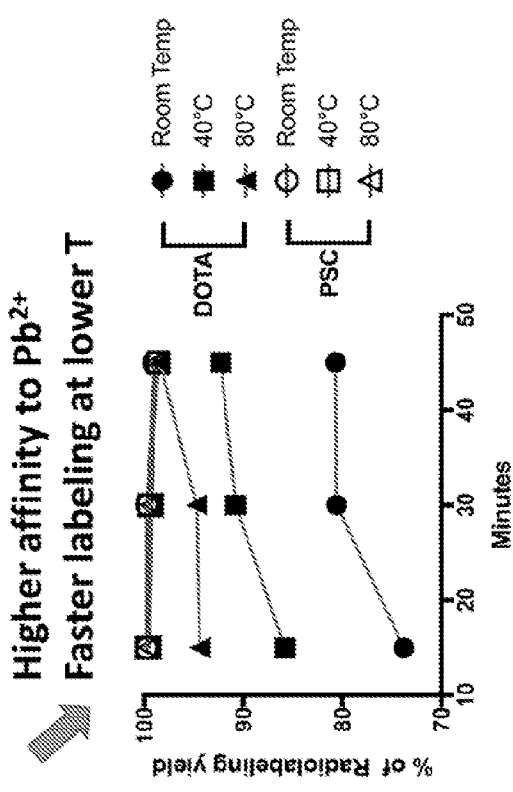
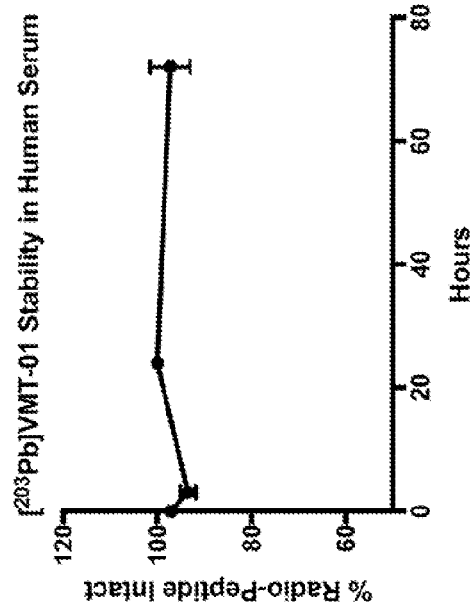

Figure 11
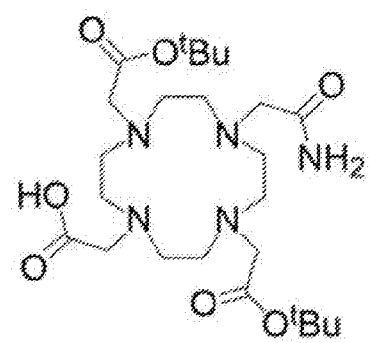
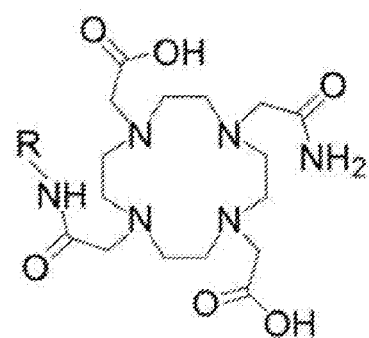
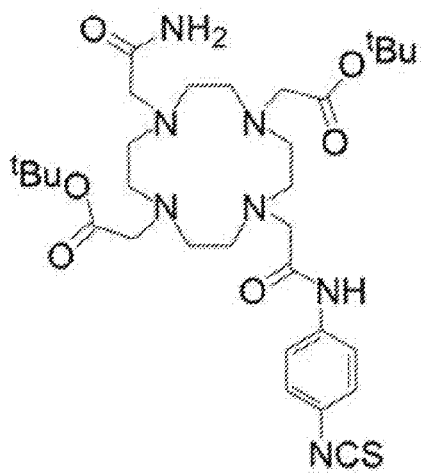
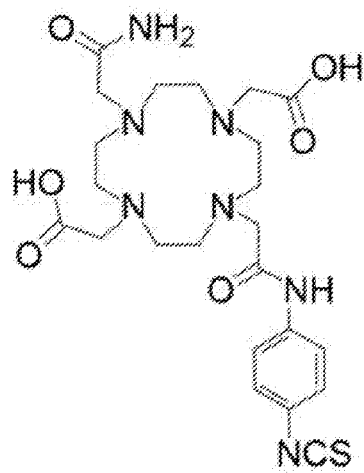

Figure 12

Protected carboxy groups

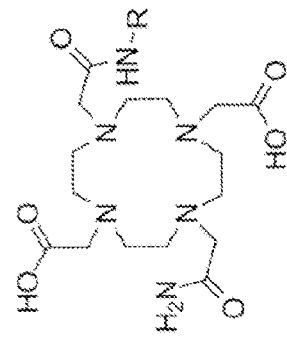

2-(7-(2-amino-2-oxoethyl)-4,10-bis(2-(tert-butoxy)-2-oxoethyl)-1,4,7,10-tetraazacyclododecan-1-yl)acetic acid

Deprotected carboxy groups

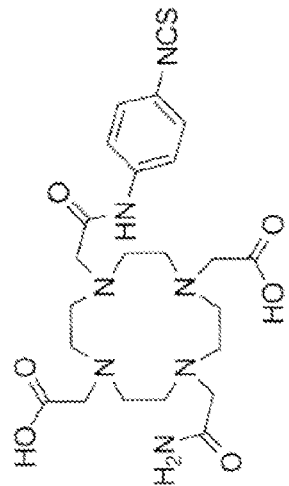

2,2'-(4-(2-amino-2-oxoethyl)-10-(2-((4-isothiocyanatophenyl)amino)-2-oxoethyl)-1,4,7,10-tetraazacyclododecane-1,7-diyl)diacetic acid

The Bn-NCS is useful for attaching to antibodies

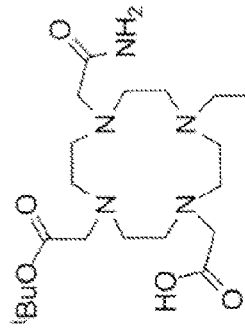

di-tert-butyl 2,2'-(4-(2-amino-2-oxoethyl)-10-(2-((4-isothiocyanatophenyl)amino)-2-oxoethyl)-1,4,7,10-tetraazacyclododecane-1,7-diyl)diacetate

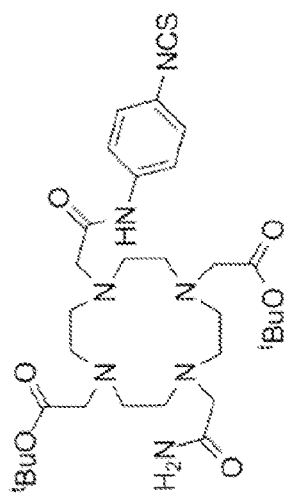

2,2'-(4-(2-amino-2-oxoethyl)-10-(2-((4-isothiocyanatophenyl)amino)-2-oxoethyl)-1,4,7,10-tetraazacyclododecane-1,7-diyl)diacetic acid R = peptide, antibody, antibody fragment, small molecule, or other molecule that is designed to bind to an protein or antigen or other structure on cells.

Figure 13

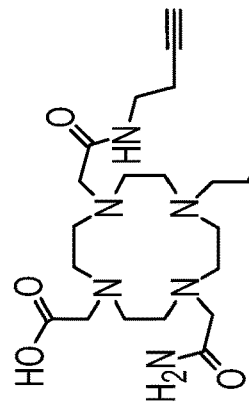

2,2'-(4-(2-amino-2-oxoethyl)-10-(2-(but-3-yn-1-ylamino)-2-oxoethyl)-1,4,7,10-tetraazacyclododecane-1,7-diyl)diacetic acid

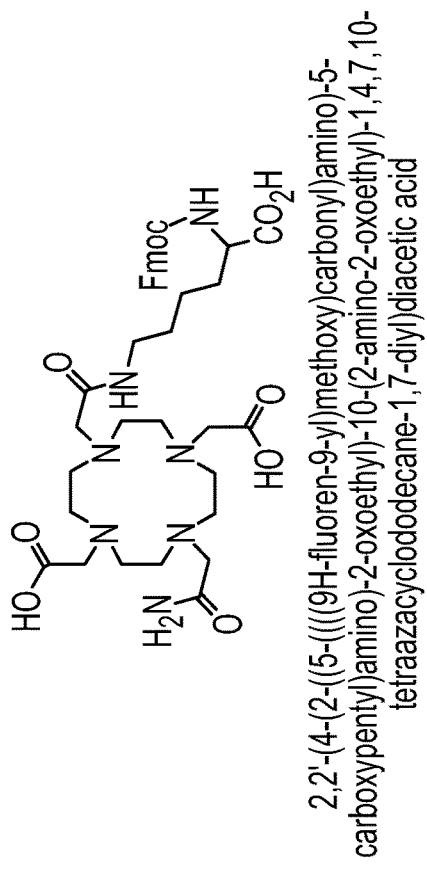

2,2'-(4-(2-((5-((((9H-fluoren-9-yl)methoxy)carbonyl)amino)-5-carboxypentyl)amino)-2-oxoethyl)-10-(2-amino-2-oxoethyl)-1,4,7,10-tetraazacyclododecane-1,7-diyl)diacetic acid

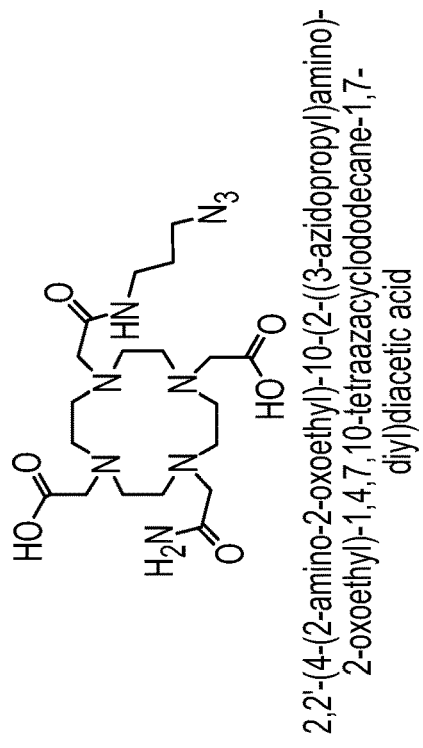

2,2'-(4-(2-amino-2-oxoethyl)-10-(2-((3-azidopropyl)amino)-2-oxoethyl)-1,4,7,10-tetraazacyclododecane-1,7-diyl)diacetic acid

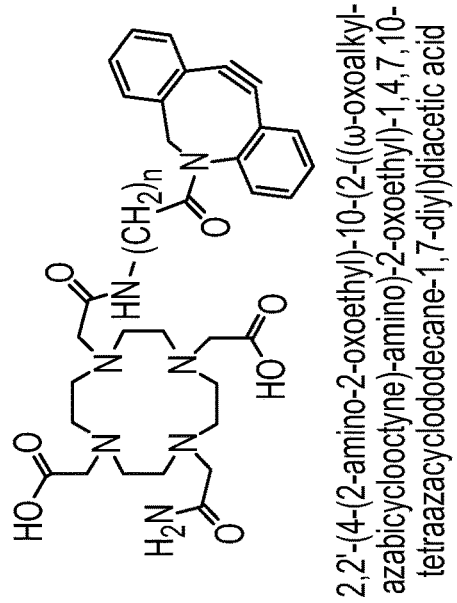

2,2'-(4-(2-amino-2-oxoethyl)-10-(2-((ω-oxoalkyl-azabicyclooctyne)-amino)-2-oxoethyl)-1,4,7,10-tetraazacyclododecane-1,7-diyl)diacetic acid (3S,10S,14S)-1-(((1R,4S)-4-(((R)-6-(2-(7-(2-amino-2-oxoethyl)-4,10-bis(carboxymethyl)-1,4,7,10-tetraazacyclododecan-1-yl)acetamido)-2-(4-(4-iodophenyl)butanamido)hexanamido)methyl)cyclohexyl)-3-(naphthalen-2-ylmethyl)-1,4,12-trioxo-2,5,11,13-tetraazahexadecane-10,14,16-tricarboxylic acid (3S,10S,14S)-1-((1r,4S)-4-((2-(7-(2-amino-2-oxoethyl)-4,10-bis(carboxymethyl)-1,4,7,10-tetraazacyclododecan-1-yl)acetamido)methyl)cyclohexyl)-3-(naphthalen-2-ylmethyl)-1,4,12-trioxo-2,5,11,13-tetraazahexadecane-10,14,16-tricarboxylic acid (15S,19S)-1-(7-(2-amino-2-oxoethyl)-4,10-bis(carboxymethyl)-1,4,7,10-tetraazacyclododecan-1-yl)-2,9,17-trioxo-3,10,16,18-tetraazahenicosane-15,19,21-tricarboxylic acid

COMPOSITIONS FOR CHELATING METALS AT LOW TEMPERATURES

PRIORITY APPLICATION

This application claims priority to U.S. Provisional Application No. 62/663,671 filed on Apr. 27, 2018. The entire content of the application referenced above is hereby incorporated by referenced herein.

BACKGROUND

Radioactive metals are used often for diagnostic imaging and radionuclide therapy for disease. For these purposes, radiometals are most often attached to molecules that are often referred to as "ligands." These ligands can be antibodies, aptamers, peptides, antibody fragments, or small molecules that are designed to bind specifically and with high affinity to proteins that are present in the disease, but often are not present (or at very low concentration) on normal cells. Thus, the ligand acts as a vehicle to deliver radiation (as a radioactive metal) to the site of malignancy in the body. For cancer diagnosis and monitoring applications, ligands deliver radioactive metals that emit photons and positrons for SPECT and PET imaging. For therapy, ligands deliver radioactive metals that emit particles such as beta and alpha particles or auger electrons. In most cases, the attachment of the radiometal to the ligand requires a modification of the ligand to include a molecular structure that is referred to as a chelator.

There is an on-going need for radiolabeled ligands for diagnostic and therapeutic uses.

SUMMARY

In certain embodiments, the present invention provides a method of performing a chelating reaction comprising contacting a divalent metal with a compound of Formula (I):

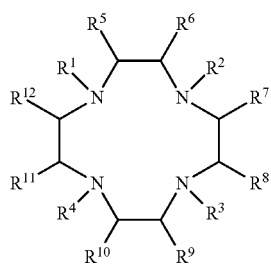

(I)

or a salt thereof wherein:
each of $R^1$-$R^4$ is independently selected from the group consisting of $CH_2COOR^a$ and $CH_2C(=O)NHR^a$;
each of $R^5$-$R^{12}$ is independently selected from the group consisting of H and -L-X;
each $R^a$ is independently selected from the group consisting of H and -L-X;
each L is independently selected from the group consisting of absent and a linking group; and
each X is a biological agent or ligand; and
wherein the contacting occurs at a temperature below about 40° C. to form a chelated composition.

In certain embodiments, the present invention provides a method of diagnosing a disease in a patient in need thereof, comprising:

(a) performing a chelating reaction comprising contacting a divalent metal with a compound of Formula (I):

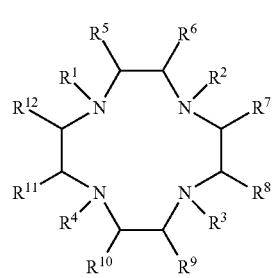

(I)

or a salt thereof wherein:
each of $R^1$-$R^4$ is independently selected from the group consisting of $CH_2COOR^a$ and $CH_2C(=O)NHR^a$;
each of $R^5$-$R^{12}$ is independently selected from the group consisting of H and -L-X;
each $R^a$ is independently selected from the group consisting of H and -L-X;
each L is independently selected from the group consisting of absent and a linking group; and
each X is a biological agent or ligand; and
wherein the contacting occurs at a temperature below about 40° C. to form a chelated composition; and (b) administering the chelated composition to the patient within two hours of the chelating reaction.

In certain embodiments, the present invention provides a method of treating a disease in a patient in need thereof, comprising administering a chelated composition to the patient within two hours of the chelated composition being chelated, wherein the chelated composition comprises a compound of Formula I chelated with a divalent metal, wherein the compound of Formula I comprises:

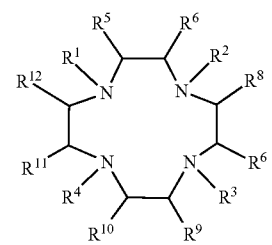

(I)

or a salt thereof wherein:
each of $R^1$-$R^4$ is independently selected from the group consisting of $CH_2COOR^a$ and $CH_2C(=O)NHR^a$;
each of $R^5$-$R^{12}$ is independently selected from the group consisting of H and -L-X;
each $R^a$ is independently selected from the group consisting of H and -L-X;
each L is independently selected from the group consisting of absent and a linking group; and
each X is a biological agent.

BRIEF DESCRIPTION OF DRAWINGS

FIG. 5. This figure provides a comparison of VMT-01 with DOTA.

FIGS. 11-15. Exemplary bifunctional structures

DETAILED DESCRIPTION

Figure 1:
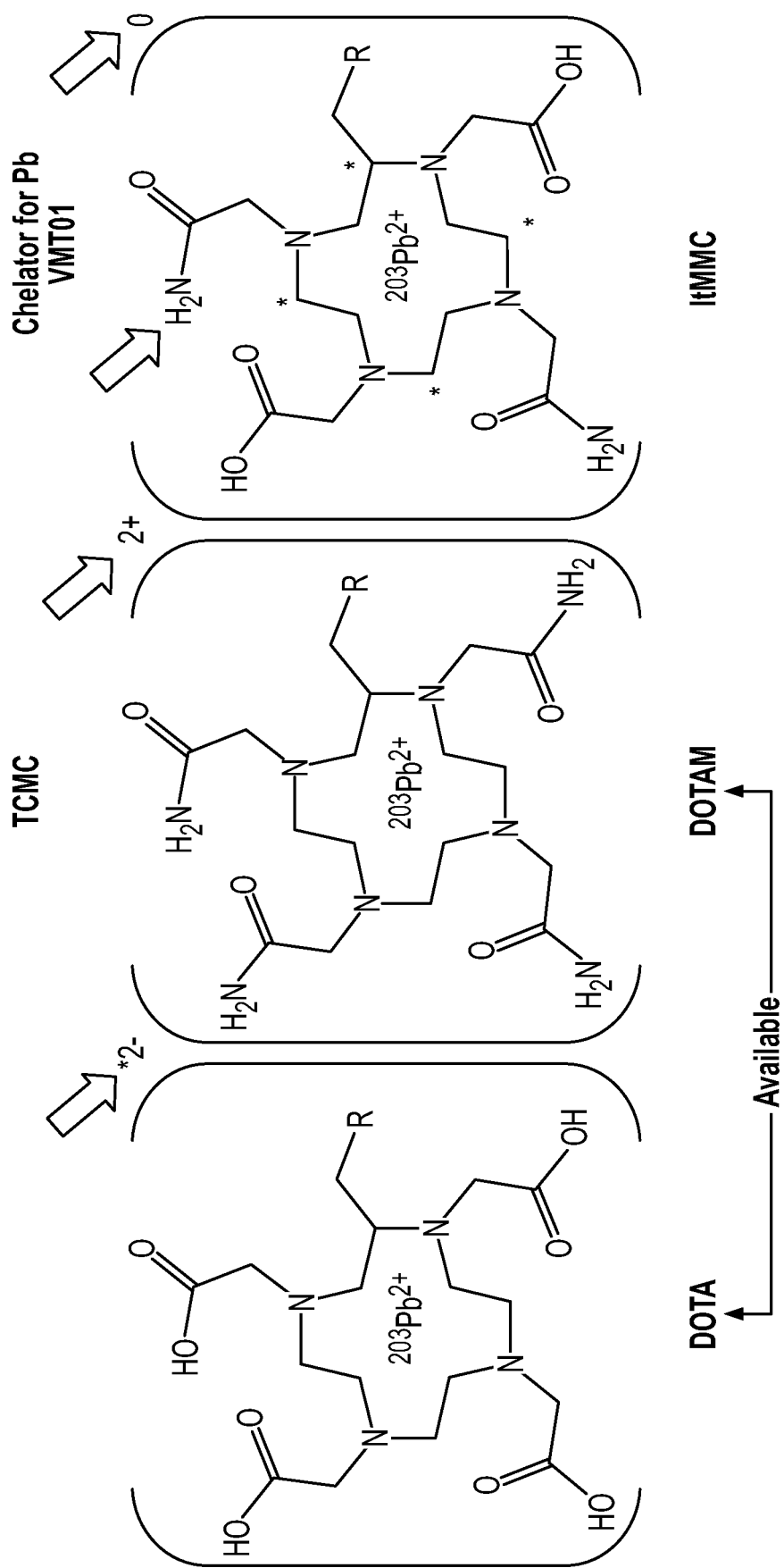
FIG. 1. Chemical structures of DOTA, DOTAM and LTMMC. DOTA has a net −2 charge, DOTAM has a net +2 charge, and LTMMC is neutral. In addition to the carboxyl and amide groups, all sites indicated with an asterisk (*) in the LTMMC can be used to link to one or more ligands.

Chelators have special properties that allow the ready attachment of radiometals to the ligand. One metallic element that is emerging as having properties that are valuable for radiometric diagnostic imaging and radionuclide therapy is lead (Pb) The reason for this is that there are two isotopes of Pb that represent a pair that can be applied for imaging (Pb-203) and therapy (Pb-212).

A chelator for Pb isotopes was developed that has surprising properties for the radiometallation reaction. While radiometallation reactions for Pb isotopes is generally carried out at temperatures greater than 80° C. (for 45 min to 2 h), a composition of matter has been newly discovered that enables Pb-203 and Pb-212 labeling at low temperatures (<37° C.) As used herein, these chelators are called "low temperature macrocyclic metal chelators" (LTMMC). Data collected to date show that the radiometallation reaction proceeds to nearly 100% completion at temperatures as low as 4° C. in 15 minutes or less. The reaction proceeds more rapidly than other chelators used for Pb reactions and the radiometal-chelator coupling is stable in serum. This is important because it allows for the radiometallation reaction with Pb isotopes to be conducted for molecules that are potentially unstable at higher temperatures needed for radiometallation of Pb isotopes and also allows for a rapid radiometallation reaction at low temperatures, which is preferred for preparation of these radiopharmaceuticals for clinical use.

The data also show that the labeling reaction happens faster than the current state of the art. The speed of the reaction at low temperatures has value particularly for radio-pharmacies, where radiopharmaceutical diagnostics and therapies are prepared for patient imaging and therapy. The speed of the reaction at room temperature makes it so that the chelator modified ligand and radiometal solutions can simply be mixed and in a few minutes, the radiometallation reaction is complete, and the radioactive drug is ready for immediate patient administration.

LTMMC Compounds

The present invention provides a molecular structure that enables radiolabeling with divalent radionuclides at low temperature. In its useful form, the invention is connected via a linker molecule to a ligand that is designed to bind to cancer cells to enable delivery of radiation for imaging and therapy to tumors.

LTMMC Chelator+Linker+Ligand

The linker is a molecule a molecular chain that connects the chelator to the ligand. In certain embodiments, the linker is polyethylene glycol, an aliphatic chain, or a polypeptide chain. The ligand is an agent of interest, such as a peptide, antibody, antibody fragment or a small molecule.

In certain embodiments, the method of the present invention chelates a compound of Formula (I):

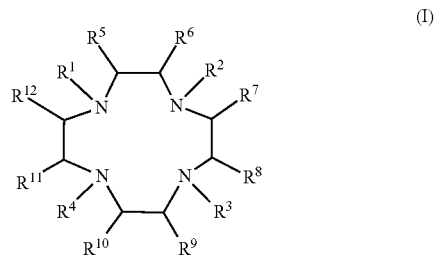

(I)

or a salt thereof wherein:
each of $R^1$-$R^4$ is independently selected from the group consisting of $CH_2COOR^a$ and $CH_2C(=O)NHR^a$;
each of $R^5$-$R^{12}$ is independently selected from the group consisting of H and -L-X;
each $R^a$ is independently selected from the group consisting of H and -L-X;
each L is independently selected from the group consisting of absent and a linking group; and
each X is a biological agent; and
wherein the contacting occurs at a temperature below about 40° C. to form a chelated composition.

In certain embodiments, two of $R^1$-$R^4$ are COORS and two of $R^1$-$R^4$ are $C(=O)NHR^a$.

In certain embodiments, the compound of formula (I) is a compound of formula (Ia):

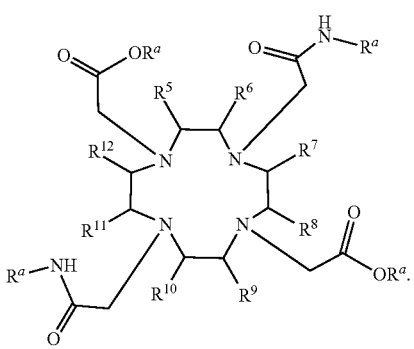

In certain embodiments, the compound of formula (I) is a compound of formula (Ib):

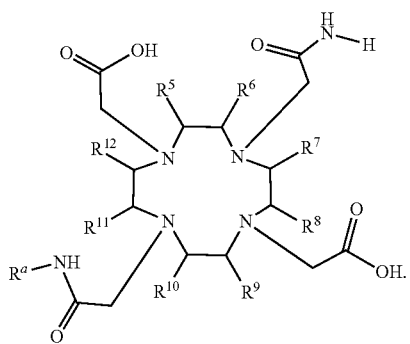

In certain embodiments, the divalent metal is lead (Pb) or copper (Cu).

In certain embodiments, the divalent metal is a radionuclide.

In certain embodiments, the radionuclide is Pb-203 or Pb-212.

In one embodiment, the LTMMC chelator has the structure:

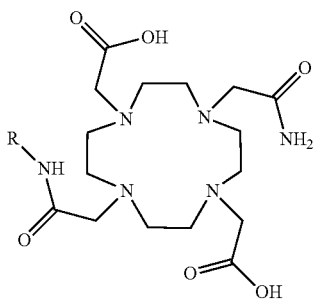

In certain embodiments, the LTMMC is radiolabeled at low temperatures with divalent metals for radionuclide imaging and therapy for cancer. For example, the LTMMC is radiolabeled with Pb-212, Pb-203, Cu-64 or Cu-67.

Figure 3A:
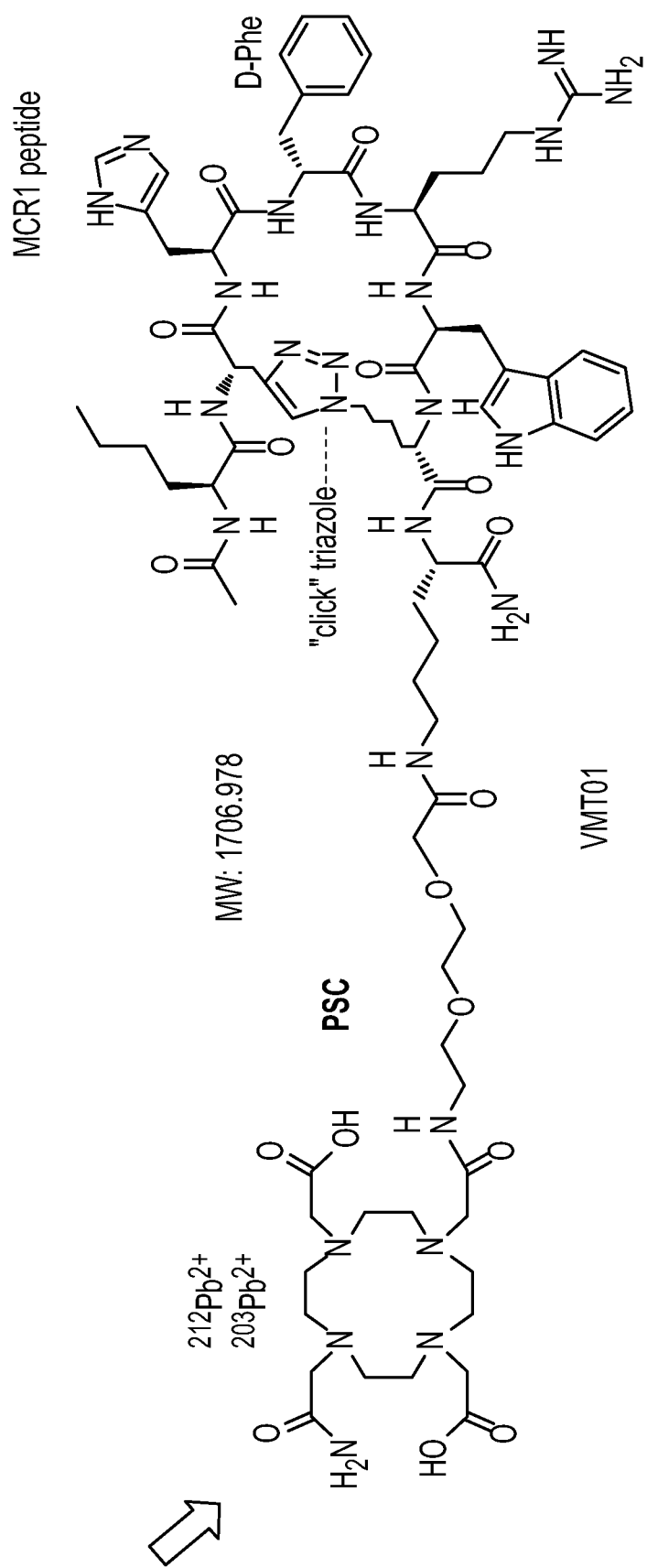
FIGS. 3A and 3B. Exemplary LTMMC structures VMT-01 (FIG. 3A) and VMT-02 (FIG. 3B).
Figure 3B:
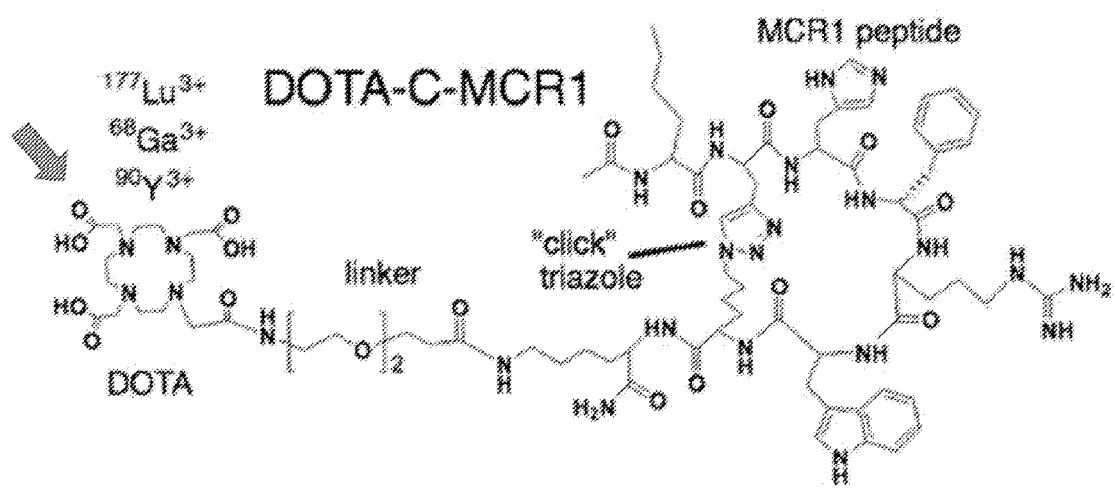

In certain embodiments, the LTMMC has the structure of VMT-01 or MVT-02 (FIGS. 3A, 3B).

In certain embodiments, exemplary bifunctional structures are provided in FIGS. 11-15.

Figure 16:
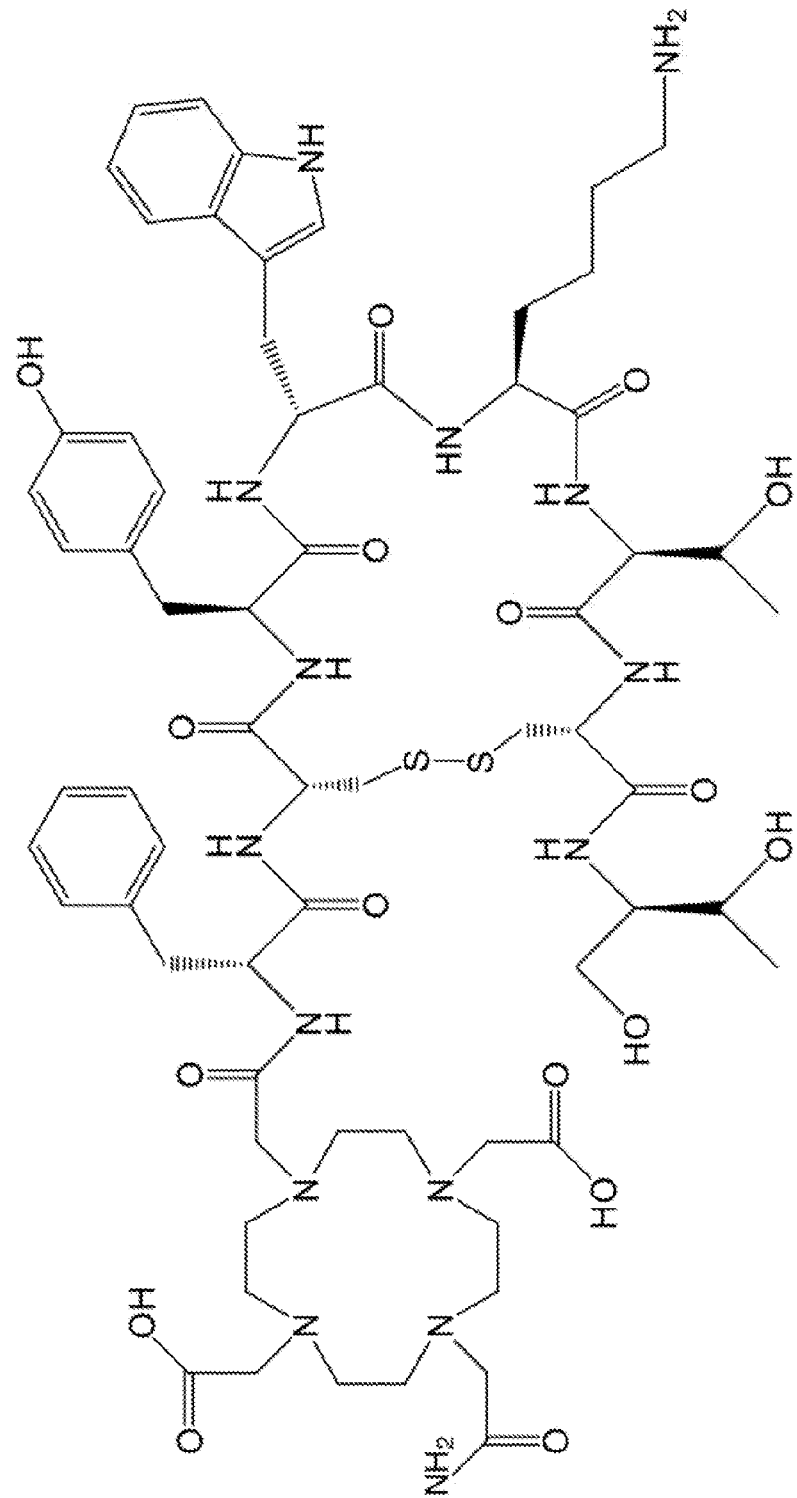
FIG. 16. Example of the PSC conjugated to a peptide, in this instance an analog of a peptide known as octreotide that is used for diagnostic imaging and therapy of cancerous tumors that express the somatostatic subtype II receptor.

In one embodiment the LTMMC was conjugated to a peptide, in this instance an analog of a peptide known as octreotide that is used for diagnostic imaging and therapy of cancerous tumors that express the somatostatic subtype II receptor. FIG. 16.

Figure 17:
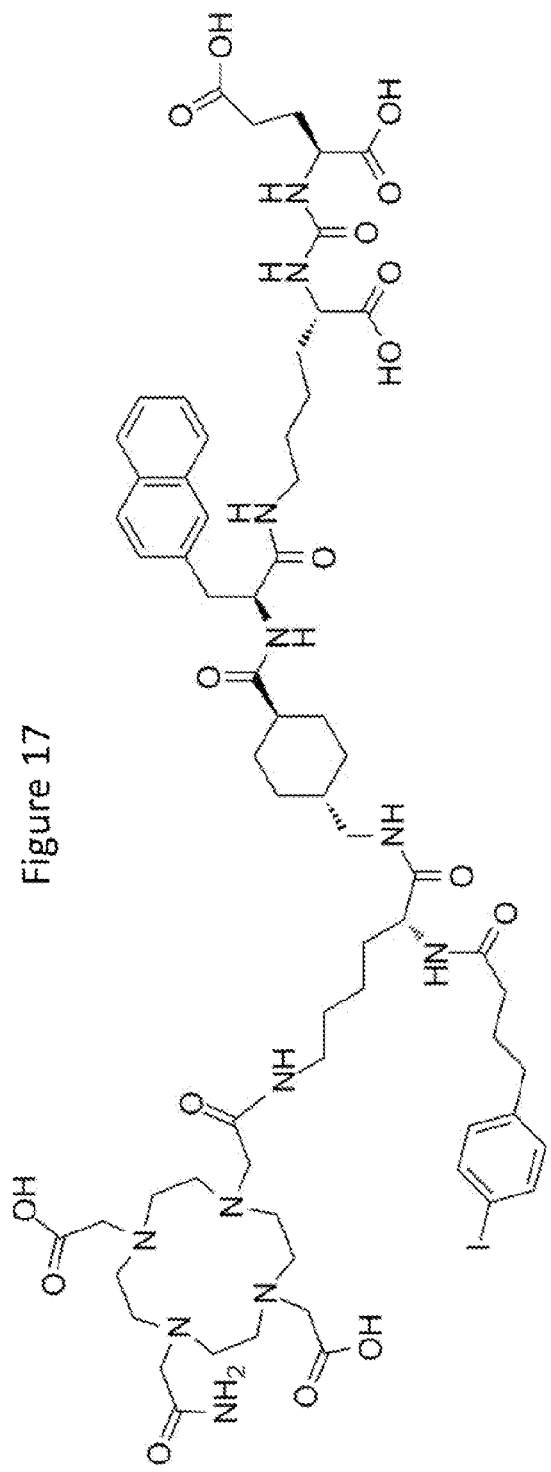
FIG. 17 provides the structure for (3S,10S,14S)-1-((1R,4S)-4-(((R)-6-(2-(7-(2-amino-2-oxoethyl)-4,10-bis(carboxymethyl)-1,4,7,10-tetraazacyclododecan-1-yl)acetamido)-2-(4-(4-iodophenyl)butanamido)hexanamido) methyl)cyclohexyl)-3-(naphthalen-2-ylmethyl)-1,4,12-trioxo-2,5,11,13-tetraazahexadecane-10,14,16-tricarboxylic acid.

FIG. 17 provides the structure for (3S,10S,14S)-1-((1R,4S)-4-(((R)-6-(2-(7-(2-amino-2-oxoethyl)-4,10-bis(carboxymethyl)-1,4,7,10-tetraazacyclododecan-1-yl)acetamido)-2-(4-(4-iodophenyl)butanamido)hexanamido)methyl)cyclohexyl)-3-(naphthalen-2-ylmethyl)-1,4,12-trioxo-2,5,11,13-tetraazahexadecane-10,14,16-tricarboxylic acid.

Figure 18:
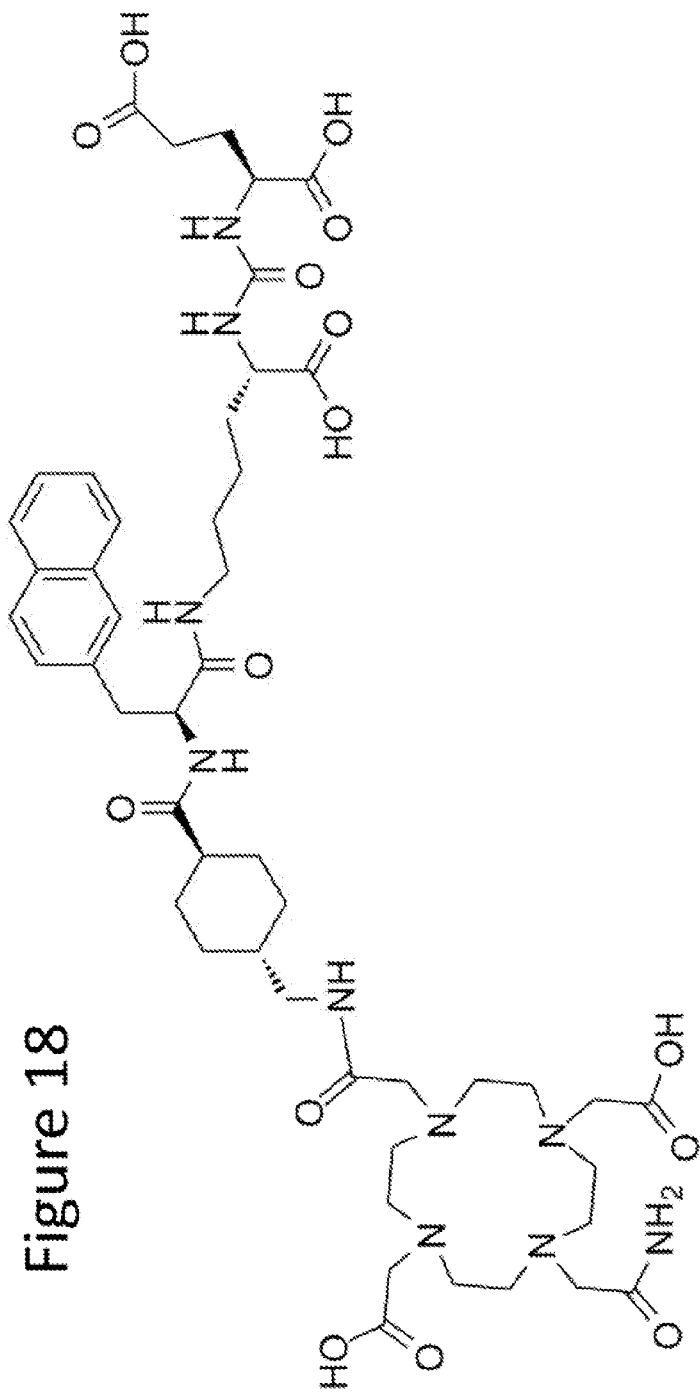
FIG. 18 provides the structure for (3S,10S,14S)-1-((1r,4S)-4-((2-(7-(2-amino-2-oxoethyl)-4,10-bis(carboxymethyl)-1,4,7,10-tetraazacyclododecan-1-yl)acetamido) methyl)cyclohexyl)-3-(naphthalen-2-ylmethyl)-1,4,12-trioxo-2,5,11,13-tetraazahexadecane-10,14,16-tricarboxylic acid FIG. 19 provides the structure for (15S,19S)-1-(7-(2-amino-2-oxoethyl)-4,10-bis(carboxymethyl)-1,4,7,10-tetraazacyclododecan-1-yl)-2,9,17-trioxo-3,10,16,18-tetraazahenicosane-15,19,21-tricarboxylic acid FIG. 20. LTMMC-VMT-01 was radiolabeled with $^{64}Cu^{2+}$ under room temperature. 1 nmol of PSC-VMT-01 was radiolabeled with 37 KBq of $^{64}Cu^{2+}$ under 25-80° C. for 10-30 minutes. Radiolabeling yield was verified by instant thin layer chromatography (iTLC). Experiments were duplicated (N=2).

FIG. 18 provides the structure for (3S,10S,14S)-1-((1r,4S)-4-((2-(7-(2-amino-2-oxoethyl)-4,10-bis(carboxymethyl)-1,4,7,10-tetraazacyclododecan-1-yl)acetamido)methyl)cyclohexyl)-3-(naphthalen-2-ylmethyl)-1,4,12-trioxo-2,5,11,13-tetraazahexadecane-10,14,16-tricarboxylic acid.

Figure 19:
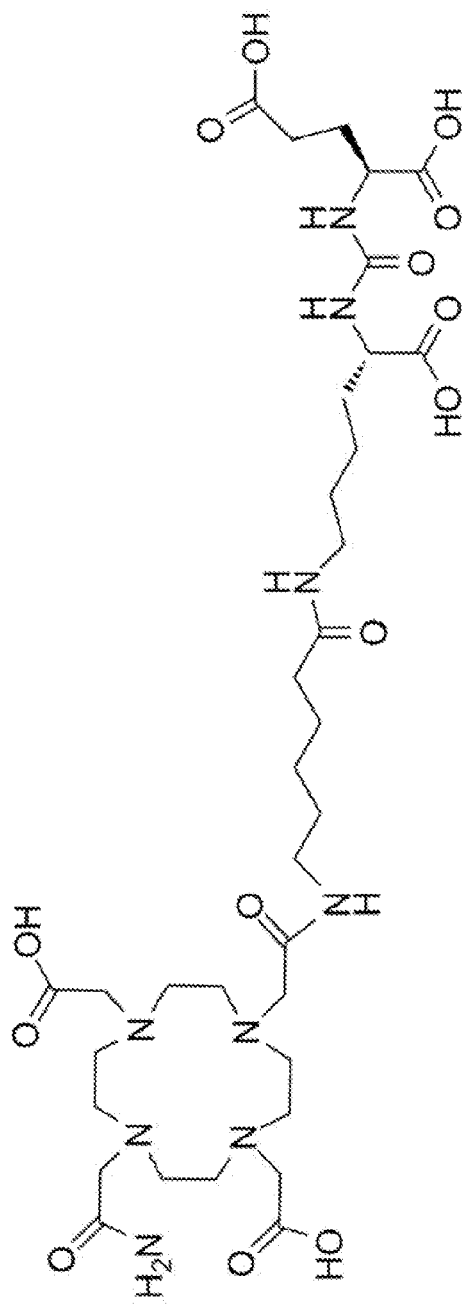

FIG. 19 provides the structure for (15S,19S)-1-(7-(2-amino-2-oxoethyl)-4,10-bis(carboxymethyl)-1,4,7,10-tetraazacyclododecan-1-yl)-2,9,17-trioxo-3,10,16,18-tetraazahenicosane-15,19,21-tricarboxylic acid.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., $(C_3-C_5)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g., tricyclic and tetracyclic carbocycles with up to about 20 carbon atoms). The rings of the multiple condensed ring system can be connected to each other via fused, Spiro and bridged bonds when allowed by valency requirements. For example, multicyclic carbocyles can be connected to each other via a single carbon atom to form a Spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, Spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein a wavy line "$\sim$" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Linking Group L

In certain embodiments of the invention L is a linking group that joins the remainder of the compound of formula I to a biological agent. The nature of the linking group L is not critical provided the resulting conjugate retains the useful biological propertied described herein.

In one embodiment of the invention the linking group has a molecular weight of from about 20 daltons to about 20,000 daltons.

In one embodiment of the invention the linking group has a molecular weight of from about 20 daltons to about 5,000 daltons.

In one embodiment of the invention the linking group has a molecular weight of from about 20 daltons to about 1,000 daltons.

In one embodiment of the invention the linking group has a molecular weight of from about 20 daltons to about 200 daltons.

In another embodiment of the invention the linking group has a length of about 5 angstroms to about 60 angstroms.

In another embodiment of the invention the linking group separates the antigen from the remainder of the compound of formula I by about 5 angstroms to about 40 angstroms, inclusive, in length.

In another embodiment of the invention the linking group is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 25 carbon atoms, wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms, wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms.

In another embodiment of the invention the linking group is a divalent, branched or unbranched, saturated hydrocarbon chain, having from 2 to 10 carbon atoms.

In another embodiment of the invention the linking group is a divalent, unbranched, saturated hydrocarbon chain, having from 2 to 10 carbon atoms.

In another embodiment of the invention the linking group is a divalent, unbranched, saturated hydrocarbon chain, having from 2 to 6 carbon atoms.

In another embodiment of the invention the linking group is a divalent, unbranched, saturated hydrocarbon chain, having from 2 to 4 carbon atoms.

In another embodiment of the invention the linking group comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the linking group is a divalent radical formed from a protein.

In another embodiment of the invention the linking group is a divalent radical formed from a peptide.

In another embodiment of the invention the linking group is a divalent radical formed from an amino acid.

In certain embodiments, L is polyethylene glycol, an aliphatic chain, or a polypeptide chain.

Other linkders are known in the art. See, e.g., Bandari R P, Jiang Z, Reynolds T S, Bernskoetter N E, Szczodroski A F, Bassuner K J, Kirkpatrick D L, Rold T L, Sieckman G L, Hoffman T J, Connors J P, Smith C J. Synthesis and biological evaluation of copper-64 radiolabeled [DUPA-6-Ahx-(NODAGA)-5-Ava-BBN(7-14)NH2], a novel bivalent targeting vector having affinity for two distinct biomarkers (GRPr/PSMA) of prostate cancer. Nucl Med Biol. 2014; 41(4):355-363. doi: 10.1016/j.nucmedbio.2014.01.001. PubMed PMID: 24508213; PMCID:PMC4041584; Dumont R A, Tamma M, Braun F, Borkowski S, Reubi J C, Maecke H, Weber W A, Mansi R. Targeted radiotherapy of prostate cancer with a gastrin-releasing peptide receptor antagonist is effective as monotherapy and in combination with rapamycin. J Nucl Med. 2013; 54(5):762-769. doi: 10.2967/jnumed.112.112169. PubMed PMID: 23492884; Gourni E, Mansi R, Jamous M, Waser B, Smerling C, Burian A, Buchegger F, Reubi J C, Maecke H R. N-terminal modifications improve the receptor affinity and pharmacokinetics of radiolabeled peptidic gastrin-releasing peptide receptor antagonists: examples of 68Ga- and 64Cu-labeled peptides for PET imaging. J Nucl Med. 2014; 55(10):1719-1725. doi: 10.2967/jnumed.114.141242. PubMed PMID: 25146125; Jamous M, Tamma M L, Gourni E, Waser B, Reubi J C, Maecke H R, Mansi R. PEG spacers of different length influence the biological profile of bombesin-based radiolabeled antagonists. Nucl Med Biol. 2014; 41(6):464-470. doi: 10.1016/j.nucmedbio.2014.03.014. PubMed PMID: 24780298; Mansi R, Abiraj K, Wang X, Tamma M L, Gourni E, Cescato R, Berndt S, Reubi J C, Maecke H R. Evaluation of three different families of bombesin receptor radioantagonists for targeted imaging and therapy of gastrin releasing peptide receptor (GRP-R) positive tumors. J Med Chem. 2015; 58(2):682-691. doi: 10.1021/jm5012066. PubMed PMID: 25474596; Pan D, Xu Y P, Yang R H, Wang L, Chen F, Luo S, Yang M, Yan Y. A new (68)Ga-labeled BBN peptide with a hydrophilic linker for GRPR-targeted tumor imaging. Amino Acids. 2014; 46(6):1481-1489. doi: 10.1007/s00726-014-1718-y. PubMed PMID: 24633452; Stott Reynolds T J, Schehr R, Liu D, Xu J, Miao Y, Hoffman T J, Rold T L, Lewis M R, Smith C J. Characterization and evaluation of DOTA-conjugated Bombesin/RGD-antagonists for prostate cancer tumor imaging and therapy. Nucl Med Biol. 2015; 42(2):99-108. doi: 10.1016/j.nucmedbio.2014.10.002. PubMed PMID: 25459113.

Ligands

Antibody and Antibody Fragments

The term "antibody" as used herein includes, but is not limited to, antibodies obtained from both polyclonal and monoclonal preparations, as well as the following: (i) chimeric antibody molecules (see, for example, Winter et al. (1991) Nature 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules that generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments. An antibody can be chimeric, human, humanized and/or affinity matured.

As used herein, the term "antibody" includes scFv, humanized, fully human or chimeric antibodies, single-chain antibodies, diabodies, and antigen-binding fragments of antibodies (e.g., Fab fragments). In certain embodiments, the antibody fragment does not contain the constant domain region of an antibody. In certain embodiments, the antibody fragment is less than 500 amino acids in length, such as between 200-450 amino acids in length, or less than 400 amino acids in length.

The phrases "specifically binds" when referring to a protein, "specifically immunologically cross reactive with," or simply "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

Aptamers

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars that are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine;

5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers of the invention are synthesized using conventional phosphodiester linked nucleotides and synthesized using standard solid or solution phase synthesis techniques that are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the aptamer portion binds to Human Epidermal growth factor Receptor 2 (HER2). In certain embodiments, modifications are made to the aptamer portion. Additional modifications to the aptamer portion include 2'O-methyl modification of the pyrimidines. In other embodiments, all of the nucleotides in the aptamer are 2'O-methyl modified. Alternatively, the pyrimidines, or all the nucleotides, may be modified with 2'fluoros (both pyrimidines and purines). Additional modifications to the nucleotides in the aptamer include large molecular weight conjugates like pegylation, lipid-based modifications (e.g., cholesterol) or nanoparticles (e.g., PEI or chitosan) to improve the pharmacokinetic/dynamic profile of the chimera.

In certain embodiments, modifications are introduced into the stem sequence in the aptamer. Different nucleotides can be used as long as the structure of the stem is retained.

Small Molecules

The compound of Formula I of the present invention can be operably linked to one or more small molecule entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a filter, magnetic bead, metal oxide, latex particle, microtiter plates, polystyrene bead, or CD-ROM.

Polypeptides

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The terms "polypeptide," "peptide," and "protein" are used interchangeably to refer to polymers of amino acids of any length. Peptides and polypeptides can be either entirely composed of synthetic, non-natural analogues of amino acids, or, is a chimeric molecule of partly natural peptide amino acids and partly non-natural analogs of amino acids. In one aspect, a polypeptide is used in a composition, cell system or process of the invention (e.g., a host cell having a plasmid expressing at least one enzyme of the invention). In addition, polypeptide can refer to compounds comprised of polymers of amino acids covalently attached to another functional group (e.g., solubilizing group, a targeting group, PEG, non-amino acid group, or other therapeutic agent).

Amino acids may be abbreviated using the following designation in parentheses: Proline (Pro), Valine (Val), Lysine (Lys), Ornithine (Orn), Norleucine (Nle), Glycine (Gly), Tryptophan (Trp), Alanine (Ala), Phenylalanine (Phe), Arginine (Arg), Histidine (His), Glutamic acid (Glu), Aspartic acid (Asp), Serine (Ser), Methionine (Met), Isoleucine (Ile), Tyrosine (Tyr), Cyclohexylalanine (Cha), 4-fluoro-D-phenylglycine (4-fluoro-D-Phg), 2-thienyl-D-alanine (D-Thi).

Polypeptide compositions of the invention can contain any combination of non-natural structural components. Individual peptide residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH2-NH), ethylene, olefin (CH=CH), ether (CH2-O), thioether (CH2-S), tetrazole, thiazole, retroamide, thioamide, or ester (see, e.g., Spatola (1983) in Chemistry and Biochemistry of Amino Acids, Peptides and Proteins, Vol. 7, pp. 267-357, "Peptide Backbone Modifications," Marcel Dekker, N.Y., incorporated herein by reference).

Polypeptides used to practice the method of the invention can be modified by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl terminus. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gammacarboxylation, glycosylation, GPI anchor formation, hydroxylation, iodination, methylation, myristoylation, oxidation, PEGylation, proteolytic processing, phosphorylation, prenylation, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983), incorporated herein by reference.

"Biologically active" moieties include a molecule or compound that elicits or modulates a physiological response. In one aspect, a biologically active compound stimulates melanocortin receptors, preferably MC1-receptors.

By "modulate" and "modulation" is meant that the activity of one or more proteins or protein subunits is up regulated or down regulated, such that expression, level, or activity is greater than or less than that observed in the absence of the modulator. For example, the term "modulate" can mean "inhibit" or "stimulate".

"C-terminal sequence" includes reference to the end of the amino acid chain terminated typically, but not necessarily, by a carboxyl group. The convention for writing peptide sequences is to put the C-terminal end on the right and write the sequence from N- to C-terminus. The C-terminal sequence may comprise 1 to 100 amino acids, preferably 2 to 15 amino acids, and even more preferably 3 to 10 amino acids. The C-terminal sequence may terminate with a carboxyl group or the terminus may be modified by well-known methods in the art to comprise a functional member (e.g. targeting group, retention signal, lipid, and anchor).

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Anti-Hyperproliferative Agents

The terms "cell proliferative disorder" and "proliferative disorder" refer to disorders that are associated with a measurable degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth and proliferation. Examples of cancer include, but are not limited to, carcinoma, lymphoma (e.g., Hodgkin's and non-Hodgkin's lymphoma), blastoma, sarcoma, and leukemia. More particular examples of cancers include squamous cell cancer, small-cell lung cancer, non-small cell lung cancer, adenocarcinoma of the lung, squamous carcinoma of the lung, cancer of the peritoneum, hepatocellular cancer, renal cell carcinoma, gastrointestinal cancer, gastric cancer, esophageal cancer, pancreatic cancer, glioma, cervical cancer, ovarian cancer, liver cancer, bladder cancer, hepatoma, breast cancer (e.g., endocrine resistant breast cancer), colon cancer, rectal cancer, lung cancer, endometrial or uterine carcinoma, salivary gland carcinoma, kidney cancer, liver cancer, prostate cancer, vulval cancer, thyroid cancer, hepatic carcinoma, melanoma, leukemia and other lymphoproliferative disorders, and various types of head and neck cancer.

The term "lung tumor" refers to any tumor of the lung, including but not limited to small-cell lung carcinoma and non-small cell lung carcinoma, the latter including but not limited to adenocarcinoma, squamous carcinoma, and large cell carcinoma.

The term "neoplasm" or "neoplastic cell" refers to an abnormal tissue or cell that proliferates more rapidly than corresponding normal tissues or cells and continues to grow after removal of the stimulus that initiated the growth.

A "lung tumor cell" refers to a lung tumor cell, either in vivo or in vitro, and encompasses cells derived from primary lung tumors or metastatic lung tumors, as well as cell lines derived from such cells.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "anti-cancer agent" includes therapeutic agents that kill cancer cells; slow tumor growth and cancer cell proliferation; and ameliorate or prevent one or more of the symptoms of cancer. An anti-cancer agent includes pharmaceutically acceptable salts. The term "pharmaceutically acceptable salts" refers to salts that retain the desired biological activity of the above-identified compounds, and include pharmaceutically acceptable acid addition salts and base addition salts. Suitable pharmaceutically acceptable acid addition salts may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

In certain embodiments, the anti-cancer agent is a MAPK pathway inhibitor, including but not limited to cobimetinib, dabrafenib, and/or trametinib.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The present invention provides a "substantially pure compound". The term "substantially pure compound" is used herein to describe a molecule, such as a polypeptide (e.g., a polypeptide that binds a target, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

"Treatment", "treating", "treat" or "therapy" as used herein refers to administering, to a mammal, agents that are capable of eliciting a prophylactic, curative or other beneficial effect in the individual. Treatment may additionally result in attenuating or ameliorating a disease or symptoms of a disease in a subject.

In certain embodiments, the conjugate is administered along with an additional conventional cancer therapy modality. In certain embodiments, the additional cancer therapy is chemotherapy and/or radiation. In certain embodiments, the mammal is a human.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments, the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Pharmaceutical Compositions

Administration of a compound as a pharmaceutically acceptable acid or base salt may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The dosage of the agent varies depending on age, weight, and condition of the subject. Treatment may be initiated with small dosages containing less than optimal doses, and increased until a desired, or even an optimal effect under the circumstances, is reached. In general, the dosage is about 450-600 mg/kg/day in patients weighing less than 20 kg, or 9.9-13.0 g/m$^2$/day in larger patients. Higher or lower doses, however, are also contemplated and are, therefore, within the confines of this invention. A medical practitioner may prescribe a small dose and observe the effect on the subject's symptoms. Thereafter, he/she may increase the dose if suitable. In general, agent is administered at a concentration that affords effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include oral, parenteral, e.g., intravenous, slow infusion, intradermal, subcutaneous, oral (e.g., ingestion or inhalation), transdermal (topical), transmucosal, and rectal administration. Such compositions typically comprise the agent and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polytheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the skin.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "about" means±10%.

In certain embodiments, the present invention provides a method of performing a chelating reaction comprising contacting a divalent metal with a compound of Formula (I):

(I)

or a salt thereof wherein:
each of $R^1$-$R^4$ is independently selected from the group consisting of $CH_2COOR^a$ and $CH_2C(=O)NHR^a$;
each of $R^5$-$R^{12}$ is independently selected from the group consisting of H and -L-X;
each $R^a$ is independently selected from the group consisting of H and -L-X;
each L is independently selected from the group consisting of absent and a linking group; and
each X is a biological agent; and wherein the contacting occurs at a temperature below about 40° C. to form a chelated composition.

In certain embodiments, two of $R^1$-$R^4$ are COORS and two of $R^1$-$R^4$ are $C(=O)NHR^a$.

In certain embodiments, the compound of formula (I) is a compound of formula (Ia):

(Ia)

In certain embodiments, the compound of formula (I) is a compound of formula (Ib):

(Ib)

In certain embodiments, the divalent metal is lead (Pb) or copper (Cu).

In certain embodiments, the divalent metal is a radionuclide.

In certain embodiments, the radionuclide is Pb-203 or Pb-212.

In certain embodiments, L is polyethylene glycol, an aliphatic chain, or a polypeptide chain.

In certain embodiments, L is a hydrophobic linking group that includes heteroatom substitutions in the aliphatic chain.

In certain embodiments, L is a hydrophilic linking group that includes heteroatom substitutions in the aliphatic chain.

In certain embodiments, L is a mixture of hydrophilic and hydrophobic entities.

In certain embodiments, L is a mixture of hydrophilic and hydrophobic entities including piperidine insertions.

In certain embodiments, L is $PEG_n$, wherein n is 1-10.

In certain embodiments, n is 2-4.

In certain embodiments, n is 4.

In certain embodiments, L is an aliphatic (ALP) linking group of 2 or 4 carbons.

In certain embodiments, L is a piperidine (PIP) based linking group with mixed characteristics.

In certain embodiments, the biological agent is a ligand.

In certain embodiments, the ligand is a peptide, an antibody or antibody fragment, or a small molecule agent.

In certain embodiments, the temperature is between 0° C. and 40° C.

In certain embodiments, the temperature is between about 0-37° C.

In certain embodiments, the temperature is between about 0-10° C.

In certain embodiments, the temperature is about 4° C.

In certain embodiments, the chelating reaction proceeds to greater than 95% labeling in less than two hours.

In certain embodiments, the chelating reaction proceeds to greater than 95% labeling in less than 30 minutes.

In certain embodiments, the present invention provides a method of diagnosing a disease in a patient in need thereof, comprising:
(a) performing a chelating reaction comprising contacting a divalent metal with a compound of Formula (I):

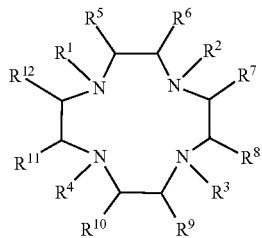

(I)

or a salt thereof wherein:

each of $R^1$-$R^4$ is independently selected from the group consisting of $CH_2COOR^a$ and $CH_2C(=O)NHR^a$;

each of $R^5$-$R^{12}$ is independently selected from the group consisting of H and -L-X;

each $R^a$ is independently selected from the group consisting of H and -L-X;

each L is independently selected from the group consisting of absent and a linking group; and each X is a biological agent; and wherein the contacting occurs at a temperature below about 40° C. to form a chelated composition; and (b) administering the chelated composition to the patient within two hours of the chelating reaction.

In certain embodiments, the present invention provides a method of treating a disease in a patient in need thereof, comprising administering achelated composition to the patient within two hours of the chelated composition being chelated, wherein the chelated composition comprises a compound of Formula I chelated with a divalent metal, wherein the compound of Formula I comprises:

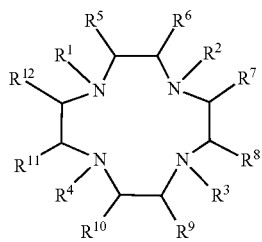

(I)

or a salt thereof wherein:

each of $R^1$-$R^4$ is independently selected from the group consisting of $CH_2COOR^a$ and $CH_2C(=O)NHR^a$;

each of $R^5$-$R^{12}$ is independently selected from the group consisting of H and -L-X;

each $R^a$ is independently selected from the group consisting of H and -L-X;

each L is independently selected from the group consisting of absent and a linking group; and each X is a biological agent.

In certain embodiments, the disease is a hyperproliferative disease.

In certain embodiments, the disease is cancer.

In certain embodiments, two of $R^1$-$R^4$ are COORS and two of $R^1$-$R^4$ are $C(=O)NHR^a$.

In certain embodiments, the compound of formula (I) is a compound of formula (Ia):

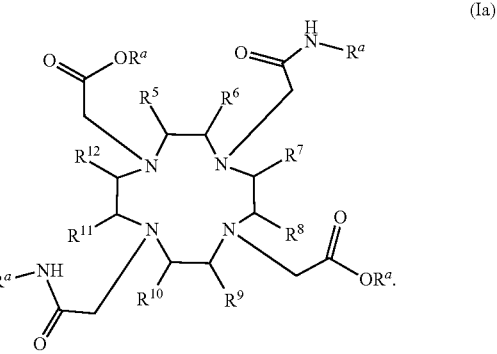

(Ia)

In certain embodiments, the compound of formula (I) is a compound of formula (Ib):

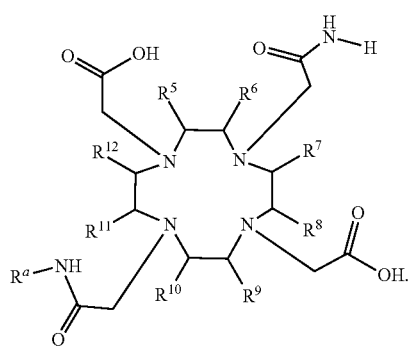

(IB)

In certain embodiments, the divalent metal is lead (Pb) or copper (Cu).

In certain embodiments, the divalent metal is a radionuclide.

In certain embodiments, the radionuclide is Pb-203 or Pb-212.

In certain embodiments, L is polyethylene glycol, an aliphatic chain, or a polypeptide chain.

In certain embodiments, L is a hydrophobic linking group that includes heteroatom substitutions in the aliphatic chain.

In certain embodiments, L is a hydrophilic linking group that includes heteroatom substitutions in the aliphatic chain.

In certain embodiments, L is a mixture of hydrophilic and hydrophobic entities.

In certain embodiments, L is a mixture of hydrophilic and hydrophobic entities including piperidine insertions.

In certain embodiments, L is $PEG_n$, wherein n is 1-10.

In certain embodiments, n is 2-4.

In certain embodiments, n is 4.

In certain embodiments, L is an aliphatic (ALP) linking group of 2 or 4 carbons.

In certain embodiments, L is a piperidine (PIP) based linking group with mixed characteristics.

In certain embodiments, the biological agent is a ligand.

In certain embodiments, the ligand is a peptide, an antibody or antibody fragment, or a small molecule agent.

In certain embodiments, the compound of Formula I is administered orally or parenterally.

In certain embodiments, the method further comprises administering an anti-cancer composition.

In certain embodiments, the compound of Formula I is administered in a single dose.

In certain embodiments, the compound of Formula I is administered in multiple doses.

In certain embodiments, the compound of Formula I is administered sequentially daily for several days.

In certain embodiments, the compound of Formula I is administered once per week for 1 month.

In certain embodiments, the compound of Formula I is administered once per week for up to 6 months.

In certain embodiments, the compound of Formula I is administered in a dose of up to 1 mCi for medical imaging.

In certain embodiments, the compound of Formula I is administered in a dose of up to 10 mCi for medical imaging.

In certain embodiments, the compound of Formula I is administered in a dose of up to 50 mCi for medical imaging.

In certain embodiments, the compound of Formula I is administered in a dose of up to 0.1 mCi for medical treatment of the cancerous tumors.

In certain embodiments, the compound of Formula I is administered in a dose of up to 1 mCi for medical treatment of the cancerous tumors.

In certain embodiments, the compound of Formula I is administered in a dose of up to 10 mCi for medical treatment of the cancerous tumors.

In certain embodiments, the compound of Formula I is administered in a dose of up to 100 mCi for medical treatment of the cancerous tumors.

In certain embodiments, the compound of Formula I is administered for more than a month.

In certain embodiments, the compound of Formula I is administered for more than a year.

In certain embodiments, the compound of Formula I is administered at a dosage of at least 1500 mg/day.

The invention will now be illustrated by the following non-limiting Examples.

Example 1

Figure 2:
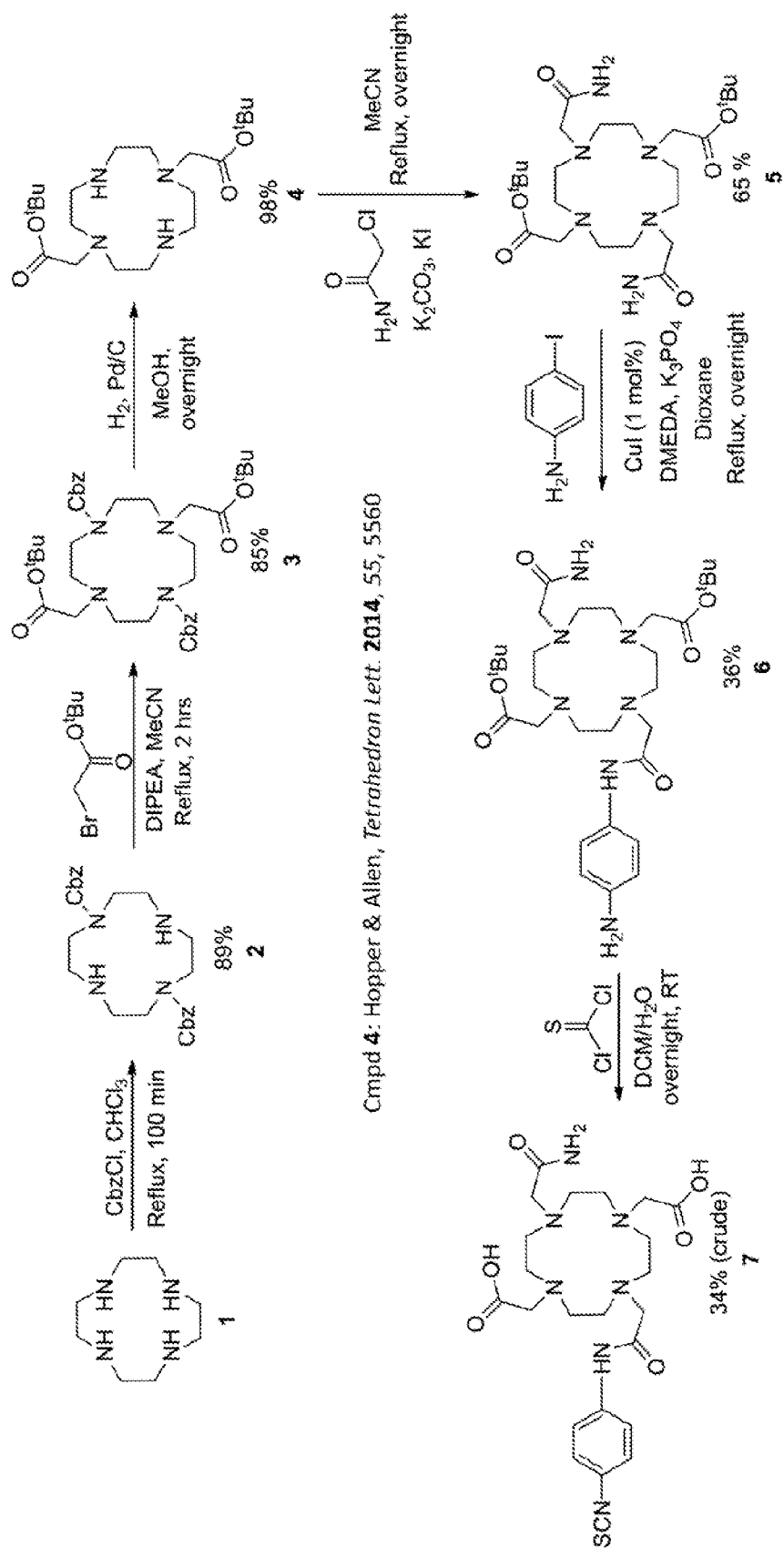
FIG. 2. Example synthesis of a 1st generation chelator with NCS functional group.

There is a need for a new low temperature macrocyclic metal chelator (LTMMC) for radiopharmaceuticals. Previous available variants result in a net formal charge and required high temperatures for labeling with metals such as Pb-203 or Pb-212. FIG. 1. Also, the reactions with the two previously-know variants (DOTA, which has a −2 charge, and DOTAM, which has a +2 charge) also take a long time to chelate (e.g., 45 min at 80° C.). This is also true for a tricarboxy DOTA, which has a −1 charge. Both DOTA and DOTAM are commercially available. A new low temperature macrocyclic metal chelator (LTMMC, also called VMT01) was synthesized, which has a neutral charge. It was possible to chelate both lead (Pb) and copper (Cu) with this compound. An example synthesis of a first-generation chelator with NCS functional group is provided in FIG. 2. Exemplary LTMMC structures are provided in FIGS. 3A, 3B (VMT_01 and VMT-02).

Figure 4:
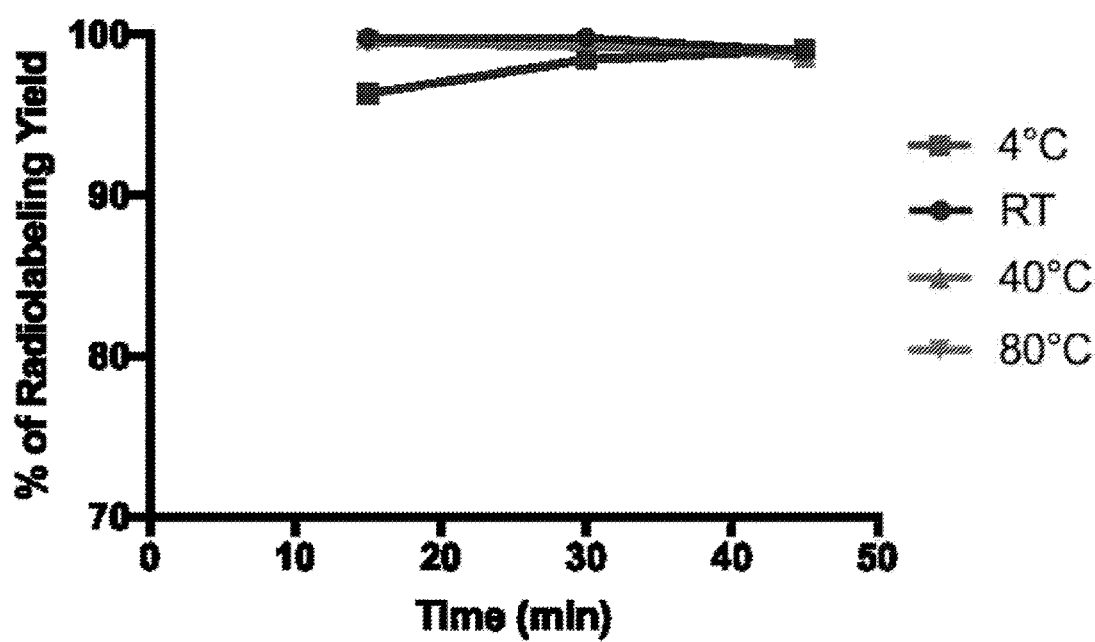
FIG. 4. Composite of Pb-203 radiolabeling efficiency. Greater than 95% labeling is achieved in 15 minutes at 4° C. (pH 5.3). For 4° C. experiments, reagents were pre-cooled for 24 h at 4° C. prior to beginning the radiolabeling reaction with PSC chelator attached to a peptide.

Radiolabeling efficiency with Pb-203 and Pb-212 was compared for these two species. It was observed that the LTMMC conjugated VMT01 labels even at 4° C. (96% in 15 minutes), which was very surprising because usually, high temperatures are required for this type of labeling using for example the DOTA-conjugated VMT02. FIG. 4.

Figure 6:
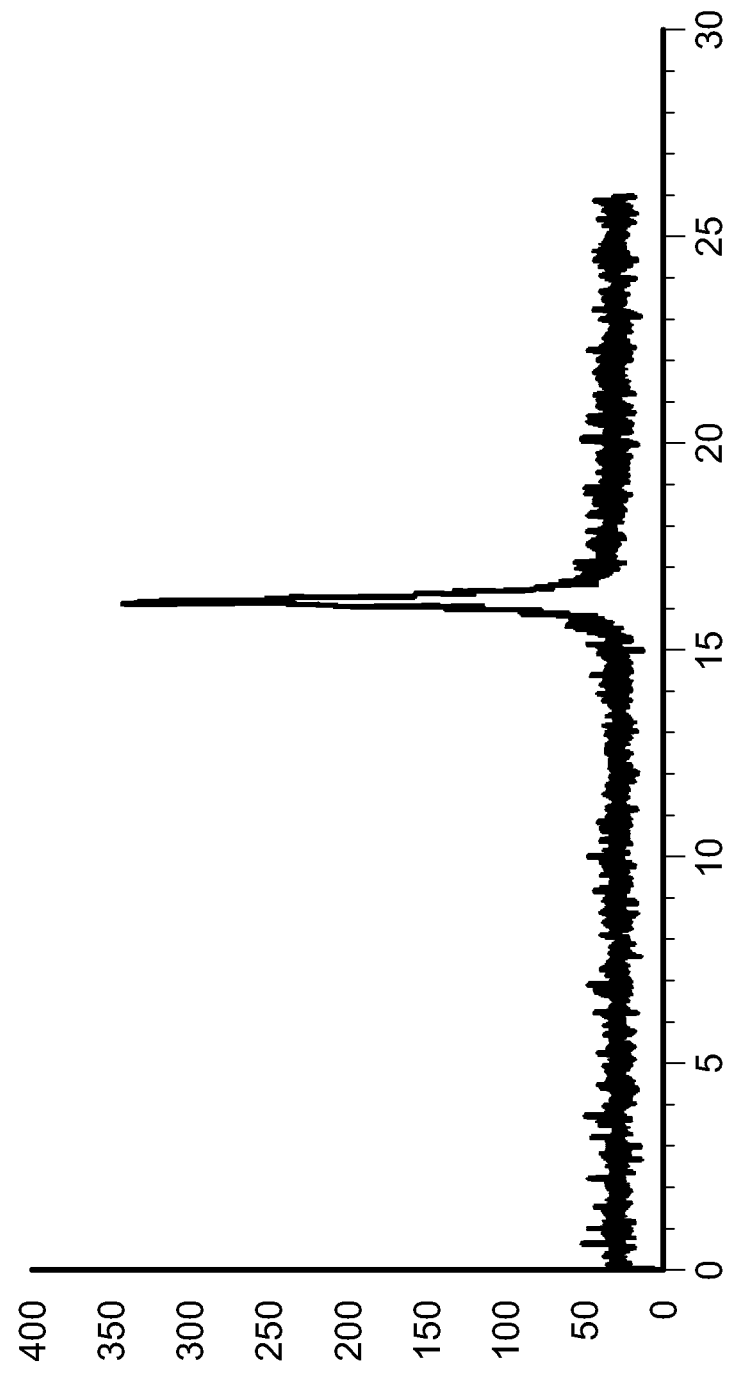
FIG. 6. Stability of VMT-01 in serum 37° C. by radio HPLC.

A study was performed to compare a LTMMC (VMT-01) with DOTA. FIG. 5. It was observed that the LTMMC labeled more quickly, and at a low temperature (>98% incorporation in 15 min). Also, the composition was stable for days in serum (37° C.). FIG. 6. It does not inhibit affinity of peptides, and was easily functionalized for peptides, mAbs, aptamers, etc. Further, commercial-scaled manufacturing was demonstrated.

Figure 7:
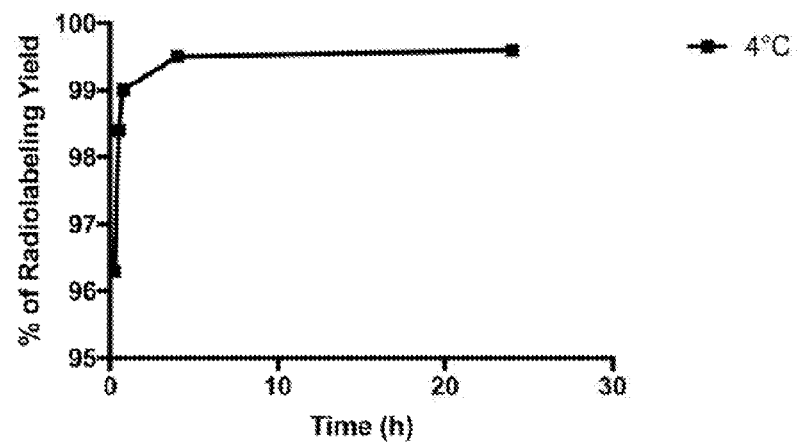
FIG. 7. Results of VMT-01 tested at 4° C.

The compound was tested at 4° C. $^{203}$Pb (1 mCi) was concentrated using methods described by Li et. al. (2017) in 400 μL pH=6 NaOAc buffer and added to 57 μL of pH=4 NaOAc buffer containing 20 μg VMT-01 peptide to achieve a final pH=5.4. The reaction vial was stored at 4° C. Instant thin layer chromatography (iTLC) imaging was applied to confirm radiolabeling efficiency. 2 μL of $^{203}$Pb labeled VMT-01 peptide and free $^{203}$Pb$^{2+}$ positive control was spotted on the iTLC strip (10 cm×2 cm) that was dried at 90° C. for at least 2 h before using. The sample strips were developed in the mobile phase 0.2M NaOAc with 20 mM EDTA. The strips were analyzed with a Typhoon FLA7000 phosphor-imager (GE Healthcare). The radiochemical purity was calculated by integrating the radioactivity counts at the solvent front ($R_f$=1) and comparing to the integrated counts at the origin ($R_f$=0) using ImageQuant Analysis Toolbox TL 7.0 (GE Healthcare). The results from the study at 4° C. are provided in FIG. 7.

Figure 8:
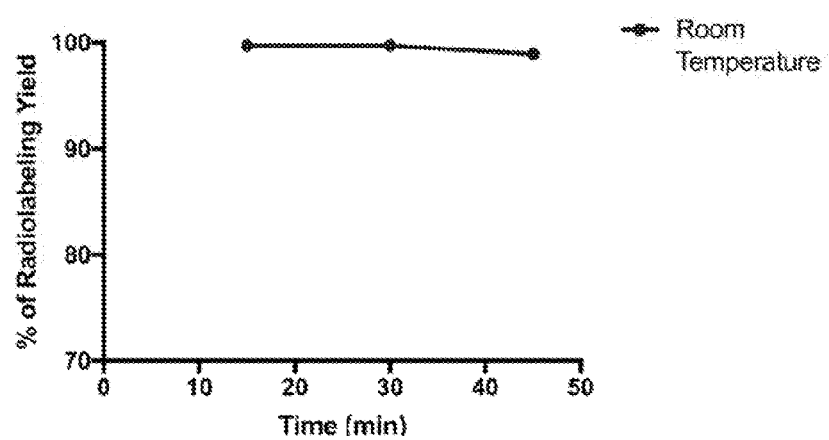
FIG. 8. Results of VMT-01 tested at room temperature.

The compound was tested at room temperature. $^{203}$Pb (0.5 mCi) was concentrated using methods described by Li et. al. (2017) in 500 μL pH=6 NaOAc buffer and added to 72.5 μL of pH=4 NaOAc buffer containing 10 μg VMT-01 peptide to achieve a final pH=5.4. The reaction vial was left on the benchtop and stored away from light. Instant thin layer chromatography (iTLC) imaging was applied to confirm radiolabeling efficiency. 2 μL of $^{203}$Pb labeled VMT-01 peptide and free $^{203}$Pb$^{2+}$ positive control was spotted on the iTLC strip (10 cm×2 cm) that was dried at 90° C. for at least 2 h before using. The sample strips were developed in the mobile phase 0.2M NaOAc with 20 mM EDTA. The strips were analyzed with a Typhoon FLA7000 phosphor-imager (GE Healthcare). The radiochemical purity was calculated by integrating the radioactivity counts at the solvent front ($R_f$=1) and comparing to the integrated counts at the origin ($R_f$=0) using ImageQuant Analysis Toolbox TL 7.0 (GE Healthcare). The results from the room temperature study are provided in FIG. 8.

Figure 9:
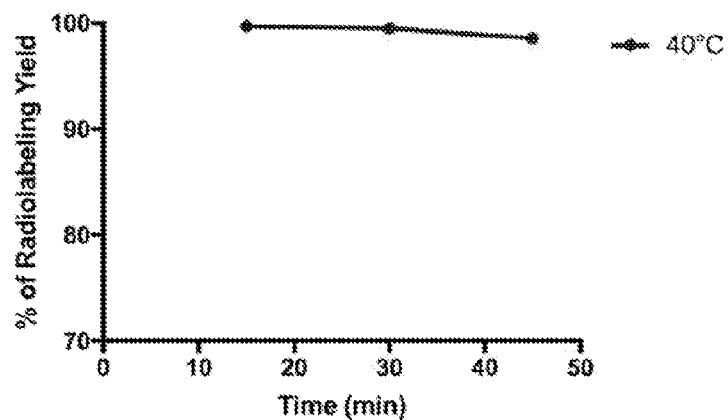
FIG. 9. Results of VMT-01 tested at 40° C.

The compound was tested at 40° C. $^{203}$Pb (0.5 mCi) was concentrated using methods described by Li et. al. (2017) in 500 μL pH=6 NaOAc buffer and added to 72.5 μL of pH=4 NaOAc buffer containing 10 μg VMT-01 peptide to achieve a final pH=5.4. The reaction vial was heated to 40° C. using a ThermoMixer. Instant thin layer chromatography (iTLC) imaging was applied to confirm radiolabeling efficiency. 2 μL of $^{203}$Pb labeled VMT-01 peptide and free $^{203}$Pb$^{2+}$ positive control was spotted on the iTLC strip (10 cm×2 cm) that was dried at 90° C. for at least 2 h before using. The sample strips were developed in the mobile phase 0.2M NaOAc with 20 mM EDTA. The strips were analyzed with a Typhoon FLA7000 phosphor-imager (GE Healthcare). The radiochemical purity was calculated by integrating the radioactivity counts at the solvent front ($R_f$=1) and comparing to the integrated counts at the origin ($R_f$=0) using ImageQuant Analysis Toolbox TL 7.0 (GE Healthcare). The results from the room temperature study are provided in FIG. 9.

Figure 10:
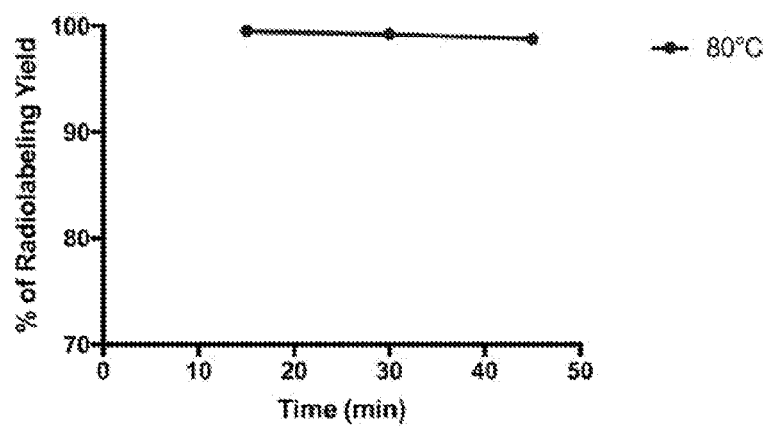
FIG. 10. Results of VMT-01 tested at 80° C.
Figure 14:
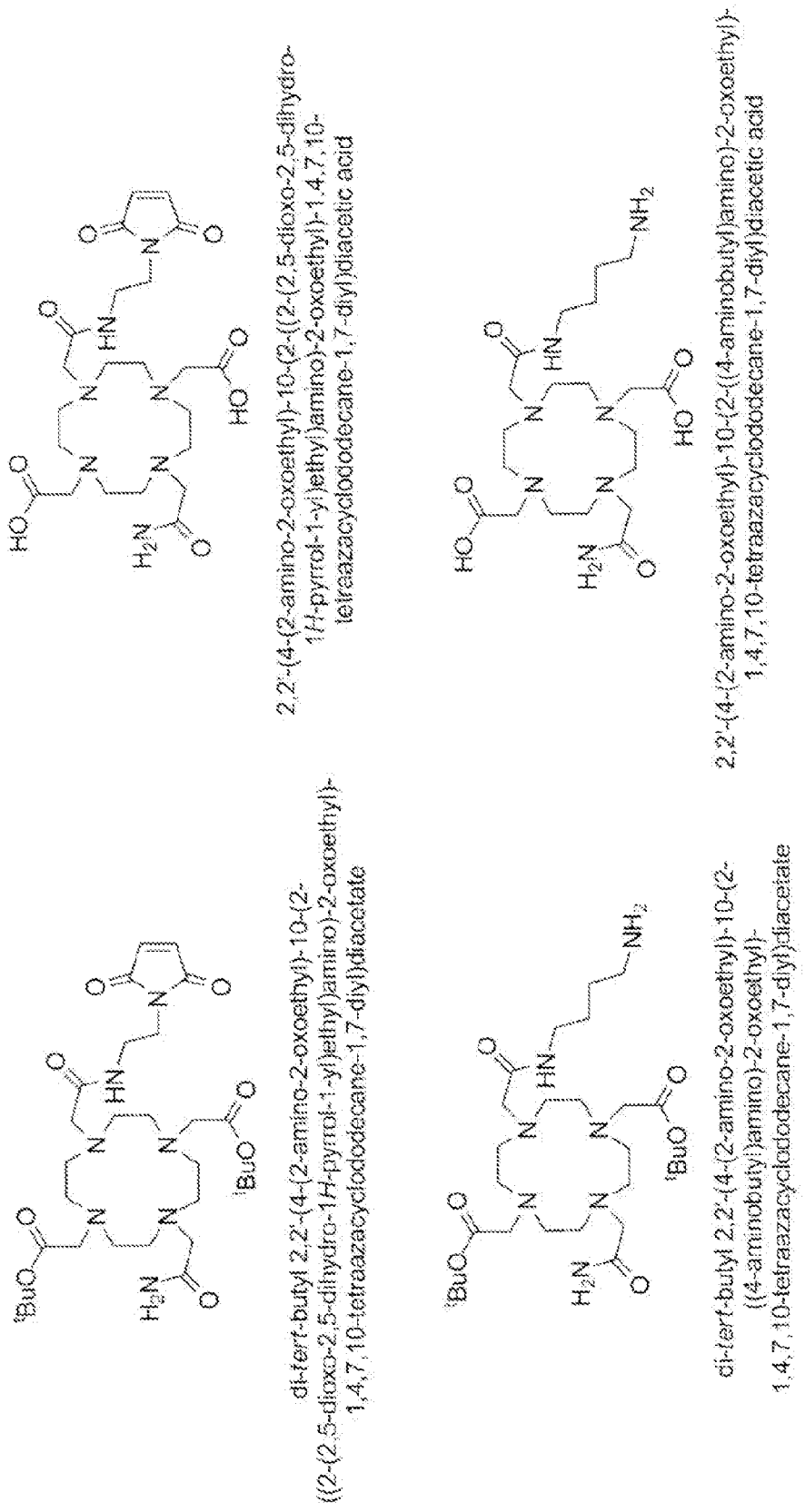
Figure 15:
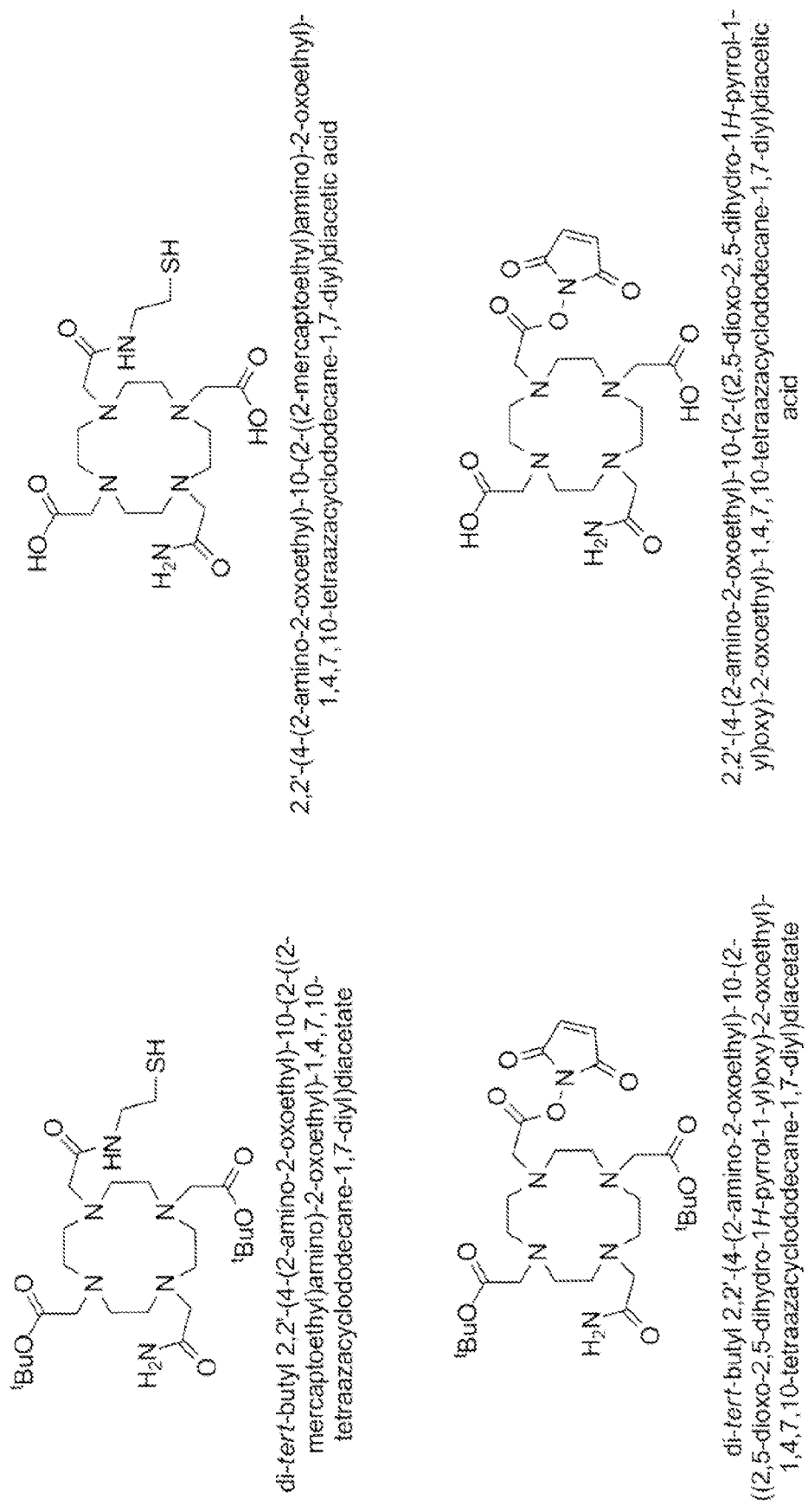

The compound was tested at 80° C. $^{203}$Pb (0.5 mCi) was concentrated using methods described by Li et. al. (2017) in 500 μL pH=6 NaOAc buffer and added to 72.5 μL of pH=4 NaOAc buffer containing 10 μg VMT-01 peptide to achieve a final pH=5.4. The reaction vial was heated to 80° C. using a ThermoMixer. Instant thin layer chromatography (iTLC) imaging was applied to confirm radiolabeling efficiency. 2 μL of $^{203}$Pb labeled VMT-01 peptide and free $^{203}$Pb$^{2+}$ positive control was spotted on the iTLC strip (10 cm×2 cm)

that was dried at 90° C. for at least 2 h before using. The sample strips were developed in the mobile phase 0.2M NaOAc with 20 mM EDTA. The strips were analyzed with a Typhoon FLA7000 phosphor-imager (GE Healthcare) The radiochemical purity was calculated by integrating the radio-activity counts at the solvent front ($R_f=1$) and comparing to the integrated counts at the origin ($R_f=0$) using ImageQuant Analysis Toolbox TL 7.0 (GE Healthcare). The results from the room temperature study are provided in FIG. 10.

Exemplary bifunctional structures are provided in FIGS. 11-15.

Figure 20:
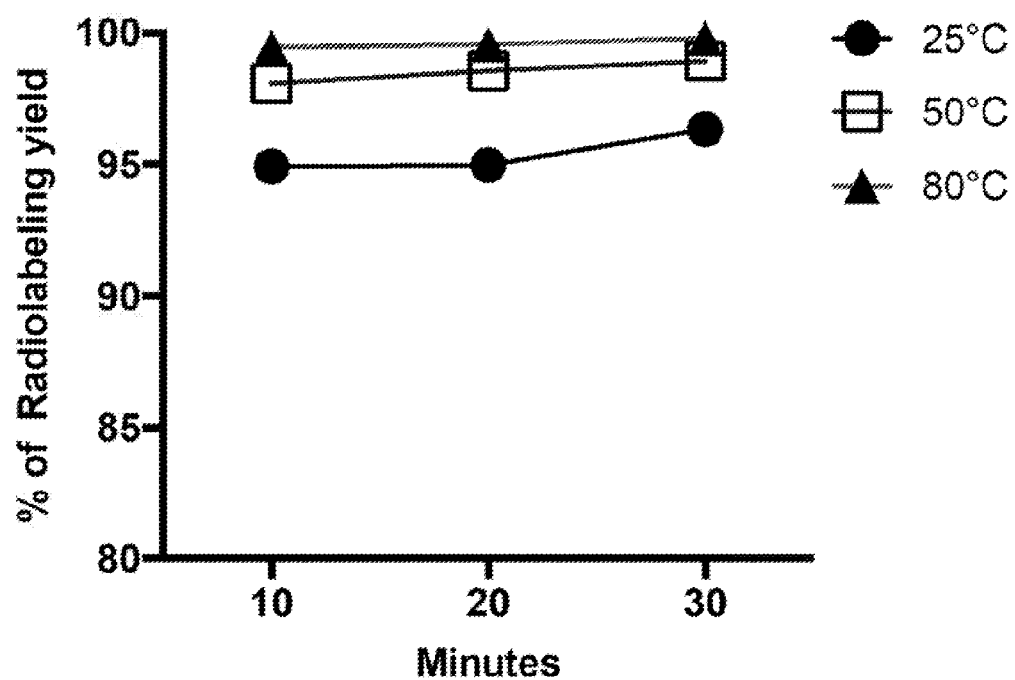

It was also observed that the chelator could be chelated at room temperature with copper radionuclides, as shown in FIG. 20.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of performing a chelating reaction comprising contacting a divalent metal with a compound of Formula (Ia):

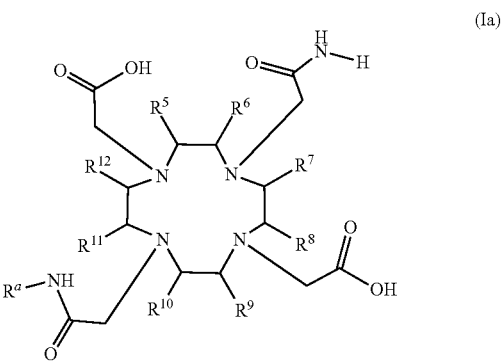

or a salt thereof wherein:
  each of $R^5$-$R^{12}$ is independently selected from the group consisting of H and -L-X;
  $R^a$ is selected from the group consisting of H and -L-X;
  each L is independently selected from the group consisting of polyethylene glycol, an aliphatic chain, and a polypeptide; and
  each X is a ligand, wherein the ligand is a peptide or a small molecule agent.

2. The method of claim 1, wherein the contacting occurs at a temperature below 40° C.

3. The method of claim 1, wherein the chelating reaction proceeds to greater than 95% labeling in less than two hours.

4. A method of diagnosing a disease in a patient in need thereof, comprising:
  (a) performing a chelating reaction comprising contacting a divalent metal with a compound of Formula (Ia):

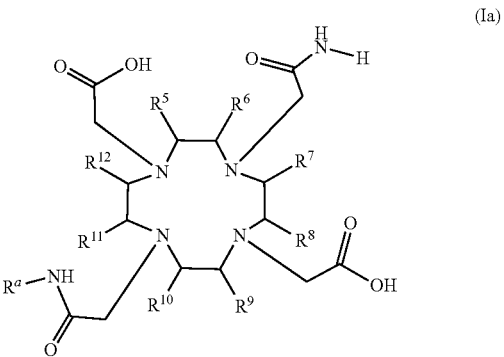

or a salt thereof wherein:
  each of $R^5$-$R^{12}$ is independently selected from the group consisting of H and -L-X;
  $R^a$ is selected from the group consisting of H and -L-X;
  each L is independently selected from the group consisting of polyethylene glycol, an aliphatic chain, or a polypeptide chain; and
  each X is a ligand, wherein the ligand is a peptide or a small molecule agent; and
  (b) administering the chelated composition to the patient.

5. A method of treating a disease in a patient in need thereof, comprising administering a chelated composition to the patient, wherein the chelated composition comprises a compound of Formula Ia chelated with a radionuclide, wherein the compound of Formula Ia comprises:

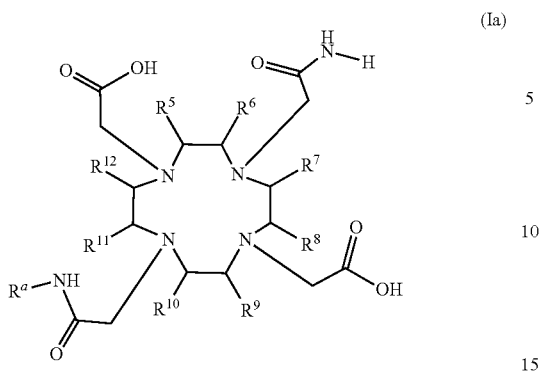

(Ia)

or a salt thereof wherein:
  each of $R^5$-$R^{12}$ is independently selected from the group consisting of H and -L-X;
  $R^a$ is selected from the group consisting of H and -L-X;
  each L is independently selected from the group consisting polyethylene glycol, an aliphatic chain, or a polypeptide chain; and
  each X is a ligand, wherein the ligand is a peptide or a small molecule agent.

6. The method of claim 4, wherein the disease is a hyperproliferative disease.

7. The method of claim 6, wherein the disease is cancer.

* * * * *

UNITED STATES PATENT AND TRADEMARK OFFICE
CERTIFICATE OF CORRECTION

| | | |
|---|---|---|
| PATENT NO. | : 12,128,115 B2 | Page 1 of 1 |
| APPLICATION NO. | : 17/051037 | |
| DATED | : October 29, 2024 | |
| INVENTOR(S) | : Michael K. Schultz et al. | |

It is certified that error appears in the above-identified patent and that said Letters Patent is hereby corrected as shown below:

In the Claims

Column 30, Lines 58-59, Claim 4, please delete "aliphatic chain, or a polypeptide" and insert -- aliphatic chain, and a polypeptide --;

Column 31, Lines 22-23, Claim 5, please delete "aliphatic chain, or a polypeptide" and insert -- aliphatic chain, and a polypeptide -- therefor.

Signed and Sealed this
Sixteenth Day of September, 2025

Coke Morgan Stewart
*Acting Director of the United States Patent and Trademark Office*